(12) United States Patent
Charo et al.

(10) Patent No.: US 7,074,770 B1
(45) Date of Patent: Jul. 11, 2006

(54) METHOD OF DNA VACCINATION

(75) Inventors: Jehad Charo, Stockholm (SE); Rolf Kiessling, Stockholm (SE)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/763,462

(22) PCT Filed: Aug. 25, 1999

(86) PCT No.: PCT/EP99/06217

§ 371 (c)(1),
(2), (4) Date: May 1, 2001

(87) PCT Pub. No.: WO00/12121

PCT Pub. Date: Mar. 9, 2000

(30) Foreign Application Priority Data

Aug. 26, 1998 (GB) ................................. 9818627.3

(51) Int. Cl.
*A01N 43/04* (2006.01)
*A61N 31/70* (2006.01)

(52) U.S. Cl. ...................................... 514/44
(58) Field of Classification Search ................... 514/44
See application file for complete search history.

(56) References Cited

U.S. PATENT DOCUMENTS 5,508,310 A * 4/1996 Rhodes ........................ 514/576
5,620,896 A * 4/1997 Herrmann et al. ........ 435/320.1
5,630,796 A * 5/1997 Bellhouse et al. ............. 604/49

FOREIGN PATENT DOCUMENTS

| WO | WO 94/07479 | 4/1994 |
| WO | WO94/07479 | 4/1994 |
| WO | WO 95/20660 | 8/1995 |

OTHER PUBLICATIONS

Rhodes J. et al.: "Therapeutic potentiation of the immune system by costimulatory Schiff-base-forming drugs see comments!." NATURE, (Sep. 1995) 377 (6544) 71-5.
Rhodes J. et al.: "Covalent chemical events in immune induction: fundamental and therapeutic aspects" Immunology Today, vol. 17, No. 9, 1996, pp. 436-441.
Sasaki S. et al.: "Comparison of intranasal and intramuscular immunization against human immunodeficiency virus type 1 with a dna-monophosphoryl lipid A adjuvant vaccine" Infection and Immunity, vol. 66, No. 2, (Feb. 1998), pp. 823-826.
Sasaki S. et al.: "Adjuvant effect of Ubenimex on a DNA vaccine for HIV-1" Clinical and Experimental Immunology, vol. 111, (Jan. 1998), pp. 30-35.

* cited by examiner

*Primary Examiner*—James Ketter
*Assistant Examiner*—Konstantina Katcheves
(74) *Attorney, Agent, or Firm*—Nixon & Vanderhye P.C.

(57) ABSTRACT

A method of vaccinating a mammal against a disease state, comprising administrating to said mammal, within an appropriate vector, a nucleotide sequence encoding an antigenic peptide associated with the disease state; additionally administering to said mammal a compound which enhances both humoral and cellular immune responses initiated by the antigenic peptide, the compound being selected from the list contained herein, wherein the compound is preferably Tucaresol or a physiologically acceptable salt or ester thereof, where appropriate.

33 Claims, 13 Drawing Sheets

FIG. 1  3 days after primary immunisation

EFFECT OF TUCARESOL ON TUMOR OUTGROWTH INHIBITION IN VIVO FOLLOWING IMMUNISATION WITH A PLASMID EXPRESSING A EPSTEIN BARR VIRUS NUCLEAR ANTIGEN 4 (EBNA-4)

EFFECT OF TUCARESOL ON CTL CYTOKINE RESPONSE INDUCED BY GENE GUN DNA IMMUNISATION IN MICE

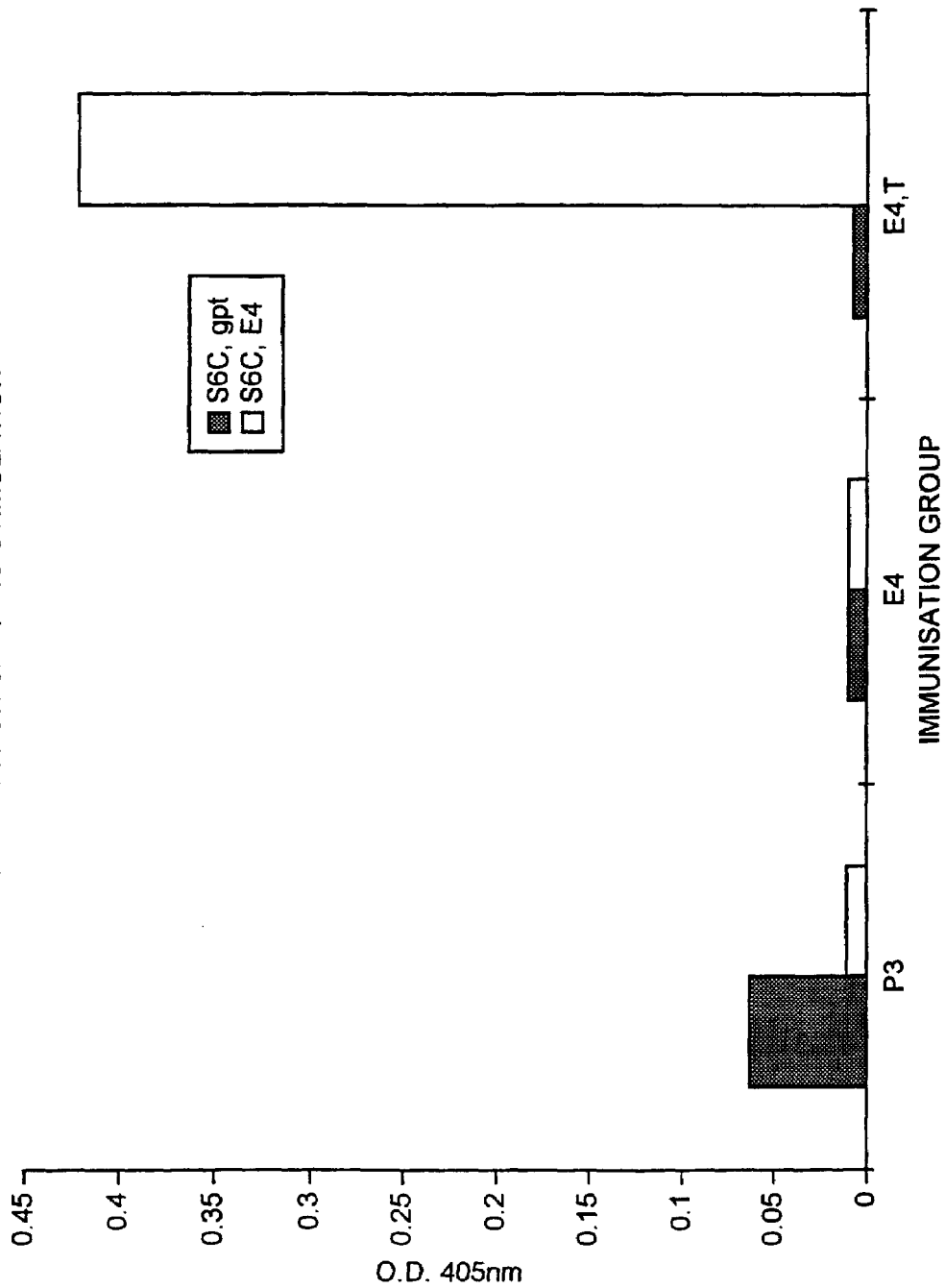

EFFECT OF TUCARESOL ADMINISTERED SUBCUTANEOUSLY ON LYTIC CTL
RESPONSE INDUCED BY GENE GUN DNA IMMUNISATION

EFFECT OF TUCARESOL ADMINISTERED ORALLY ON LYTIC CTL RESPONSE INDUCED BY GENE GUN DNA IMMUNISATION

METHOD OF DNA VACCINATION

This is a national stage application under 35 U.S.C. 371 of PCT/EP99/06217, filed Aug. 25, 1999, now abandoned.

FIELD OF THE INVENTION

The present invention relates to improvements in DNA vaccination and in particular, but not exclusively, to methods of vaccinating a mammal against disease states, to vaccine compositions and to the use of certain compounds in the manufacture in medicaments.

BACKGROUND OF THE INVENTION

Traditional vaccination techniques which involve the introduction into an animal system of an antigen which can induce an immune response in the animal, and thereby protect the animal against infection, have been known for many years. Following the observation in the early 1990's that plasmid DNA could directly transfect animal cells in vivo, significant research efforts have been undertaken to develop vaccination techniques based upon the use of DNA plasmids to induce immune responses, by direct introduction into animals of DNA which encodes for antigenic peptides. Such techniques, which are referred to as "DNA immunisation" or "DNA vaccination" have now been used to elicit protective antibody (humoral) and cell-mediated (cellular) immune responses in a wide variety of pre-clinical models for viral, bacterial and parasitic diseases.

Research is also underway in relation the use of DNA vaccination techniques in treatment and protection against cancer, allergies and autoimmune diseases.

DNA vaccines usually consist of a bacterial plasmid vector into which is inserted a strong viral promoter, the gene of interest which encodes for an antigenic peptide and a polyadenylation/transcriptional termination sequence. The gene of interest may encode a full protein or simply an antigenic peptide sequence relating to the pathogen, tumour or other agent which is intended to be protected against. The plasmid can be grown in bacteria, such as for example *E. coli* and then isolated and prepared in an appropriate medium, depending upon the intended route of administration, before being administered to the host. Following administration the plasmid is taken up by cells of the host where the encoded peptide is produced. The plasmid vector will preferably be made without an origin of replication which is functional in eukaryotic cells, in order to prevent plasmid replication in the mammalian host and integration within chromosomal DNA of the animal concerned.

There are a number of advantages of DNA vaccination relative to traditional vaccination techniques. Firstly, it is predicted that because the proteins which are encoded by the DNA sequence are synthesised in the host, the structure or conformation of the protein will be similar to the native protein associated with the disease state. It is also likely that DNA vaccination will offer protection against different strains of a virus, by generating cytotoxic T lymphocyte responses that recognise epitopes from conserved proteins. Furthermore, because the plasmids are taken up by the host cells where antigenic protein can be produced, a long-lasting immune response will be elicited. The technology also offers the possibility of combining diverse immunogens into a single preparation to facilitate simultaneous immunisation in relation to a number of disease states.

Helpful background information in relation to DNA vaccination is provided in (1), the disclosure of which is included herein in its entirety by way of reference.

Despite the numerous advantages associated with DNA vaccination relative to traditional vaccination therapies, there is nonetheless a desire to develop adjuvant compounds which will serve to increase the immune response induced by the protein which is encoded by the plasmid DNA administered to an animal.

One reason for this is that while DNA vaccines tend to work well in mice models, there is evidence of a somewhat weaker potency in larger species such as non-human primates (2, 3), which is thought to be predictive of the likely potency in humans. Adjuvants may also be useful to correct an inappropriate deviation of immune response from a Th1 to Th2 response which can be associated with DNA vaccination, especially when administered directly to the epidermis (4). Finally, it has been recognised that the DNA itself, through CpG motifs, may exhibit some adjuvant properties (5, 6, 7) which are prevalent in smaller animals administered DNA vaccines intramuscularly, but reduced in larger species or when small amounts of DNA are administered, such as via "gene-gun" administration.

Accordingly, it is one object of the present invention to provide adjuvant compounds which can be used in conjunction with DNA vaccination procedures. It is also an object to provide methods of improved DNA vaccination involving such adjuvants, as well as compositions including the adjuvants concerned. Other objects of the present invention will become apparent from the following detailed description thereof. To date, however, meeting these objects has proven difficult, largely due to mechanistic differences associated with DNA vaccination, as compared to traditional vaccine techniques.

The literature reports numerous instances of humoral immune responses in animal models, which result from DNA vaccination. Antibody responses have been shown against human growth hormone and human α-1 anti-trypsin (8), against influenza NP (9), against HIV Envelope protein (10), bovine herpes virus glycoprotein (11) and hepatitis B surface antigen (12), amongst others, following administration of plasmid DNA encoding therefore. Cytotoxic T-cell responses have also been demonstrated in animal models of DNA vaccination. Generation of cytotoxic T-cells has been demonstrated against NP from influenza A (13), hepatitis B surface antigen (HBs Ag) 65 and core antigen (14), and HIV Env (15, 16, 17) as a few examples. It is interesting to note, however, that helper T-cell response appears to be dependent upon the mode of plasmid DNA delivery. Intramuscular administration biases the helper T-cell response to Th1-like response, whereas administration primarily to the epidermis biases the immune response towards a Th2-like response (4). It is further noted that a number of known immunopotentiating agents have been tried in combination with DNA vaccination techniques with limited, or at best, mixed success. For example, while co-expression of GM-CSF with rabies virus glycoprotein (18) and carcinoembroytic antigen (CEA (19)), and co-expression of B7-1 and B7-2 *M. tuberculosis* HSP 65 (20) or CEA (19), all induced higher antibody titres than expression of the antigen alone, there is no report of an enhanced cellular immune response. Interestingly also, rabies virus glycoprotein when co-administered with DNA encoding interferon-γ, actually had an inhibitory effect on antibody response (18).

With this background in mind, it is most surprising to note that the present inventors report adjuvant compounds which show the dual action of not only stimulating humoral immune response, but simultaneously stimulating the cellular immune response mechanism. The compounds which have been recently shown to demonstrate this remarkable adjuvant activity in relation to DNA vaccination were disclosed in International Patent Publication No. WO94/07479, in relation to their immunopotentitory activity. One particular compound identified by the present inventors as having favourable DNA vaccine adjuvant activity is 4-(2-formyl-3-hydroxyphenoxymethyl)benzoic acid, also known as tucaresol, which was originally described in EP 0054924. None of the compounds now identified by the present inventors as being suited to act as adjuvants with DNA vaccines have previously been disclosed or suggested as demonstrating the humoral and cellular immunogenic activity which so suits them to the role as DNA vaccine adjuvants.

SUMMARY OF THE INVENTION

According to one embodiment of the present invention there is provided a method of vaccinating a mammal against a disease state, comprising administrating to said mammal, within an appropriate vector, a DNA sequence encoding an antigenic peptide associated with the disease state;
additionally administering to said mammal a compound which enhances both humoral and cellular immune responses initiated by the antigenic peptide, the compound being selected from:
4-(2-formyl-3-hydroxyphenoxymethyl)benzoic acid;
5-(2-formyl-3-hydroxyphenoxy)pentanamide;
N,N-diethyl 5-(2-formyl-3-hydroxyphenoxy)pentanamide;
N-isopropyl 5-(2-formyl-3-hydroxyphenoxy)pentanamide;
ethyl 5-(2-formyl-3-hydroxyphenoxy)pentanoate;
5-(2-formyl-3-hydroxyphenoxy)pentanonitrile;
(±)-5-(2-formyl-3-hydroxyphenoxy)-2-methylpentanoic acid;
5-(2-formyl-3-hydroxyphenoxy)-2,2-dimethylpentanoic acid;
methyl 3-(2-formyl-3-hydroxyphenoxy)methylbenzoate;
3-(2-formyl-3-hydroxyphenoxy)methylbenzoic acid;
benzyl 5-(2-formyl-3-hydroxyphenoxy)pentanoate;
5-[4-(2-formyl-3-hydroxyphenoxy)-N-butyl]tetrazole;
7-(2-formyl-3-hydroxyphenoxy)heptanoic acid;
5-(2-formyl-3-hydroxy-4-n-propoxyphenoxy)pentanoic acid;
5-(4,6-dichloro-2-formyl-3-hydroxyphenoxy)pentanoic acid;
5-(2-formyl-3-hydroxyphenoxy)-N-methylsulphonylpentanamide;
ethyl 4-(2-formyl-3-hydroxyphenoxymethyl)benzoate;
5-(4-chloro-2-formyl-3-hydroxyphenoxy)pentanoic acid;
5-(3-acetylamino-2-formylphenoxy)pentanoic acid;
Aminoguanidine;
4-(2-formyl-3-hydroxyphenoxy)butanoic acid;
6-(2-formyl-3-hydroxyphenoxy)hexanoic acid;
ethyl 4-(3-acetylaminio-2-formylphenoxymethyl)benzoate;
4-(3-acetylamino-2-formylphenoxymethyl)benzoic acid;
2-(2-formyl-3-hydroxyphenoxymethyl)benzoic acid;
5-[4-(2-formyl-3-hydroxyphenoxymethyl)phenyl]tetrazole;
5-(2-formyl-3-hydroxy-4-methoxyphenoxy)pentanoic acid;
3-(2-formyl-3-hydroxyphenoxy)propionitrile;
4-Hydroxyphenylacetaldehyde;
Phenylacetaldehyde;
4-Methoxyphenylacetaldehyde;
1-hydroxy-2-phenylpropane;
3-Phenylproponionaldeyde;
4-Nitrobenzaldehyde;
Methyl 4-formylbenzoate;
4-Chlorobenzaldehyde;
4-Methyloxybenzaldehyde;
4-Methylbenzaidehyde;
8,10-Dioxoundecanoic acid;
4,6-Dioxoheptanoic acid;
Pentanedione;
5-methoxy-1-tetralone;
6-methoxy-1-tetralone;
7-methoxy-1-tetralone;
2-tetralone;
3-hydroxy-1-(4-methoxyphenyl)-3-methyl-2-butanone;
2',4'-dihydroxy-2-(4-methoxyphenyl)acetophenone;
2-hydroxy-1-(4-methyoxyphenyl)-pent-2ene-4one;
Naringenin 4',5,6-trihydroxyflavonone;
4'-methoxy-2-(4-methoxyphenyl)acetophenone;
6,7-dihydroxycoumarin;
7-methoxy-2-tetralone;
6,7-dimethoxy-2-tetralone;
6-hydroxy-4-methylcoumarin;
Homogentisic acid gamma lactone;
6-hydroxy-1,2-naphthoquinone;
8-methoxy-2-tetralone;

and physiologically acceptable salts thereof, where appropriate.

Preferably the nucleotide sequence is a DNA sequence.
Preferably between one and seven administrations of the compound take place between about 14 days prior to and about 14 days post administration of the DNA sequence, particularly preferably between about 7 days prior to and about 7 days post administration of the DNA sequence, preferably between about 1 day prior to and 1 day post administration of the DNA sequence. Most particularly preferably administration of the compound is substantially simultaneous to administration of the DNA sequence, with optional further administrations of the compound in the days following administration of the DNA sequence.

Preferably the compound is administered at a dose of between about 0.1 mg/kg and about 100 mg/kg per administration.

Preferably the mammal is a human.
Preferably the compound is 4-(2-formyl-3-hydroxyphenoxymethyl)benzoic acid.

According to another embodiment of the invention there is provided a vaccine composition comprising a DNA sequence which encodes for an antigenic peptide associated with a disease state and is within an appropriate vector, and a compound which will enhance both humoral and cellular immune responses in a mammal which are initiated by the antigenic peptide, the compound being selected from:
4-(2-formyl-3-hydroxyphenoxymethyl)benzoic acid;
5-(2-formyl-3-hydroxyphenoxy)pentanamide;
N,N-diethyl 5-(2-formyl-3-hydroxyphenoxy)pentanamide;
N-isopropyl 5-(2-formyl-3-hydroxyphenoxy)pentanamide;
ethyl 5-(2-formyl-3-hydroxyphenoxy)pentanoate;
5-(2-formyl-3-hydroxyphenoxy)pentanonitrile;
(±)-5-(2-formyl-3-hydroxyphenoxy)-2-methylpentanoic acid;
5-(2-formyl-3-hydroxyphenoxy)-2,2-dimethylpentanoic acid;
methyl 3-(2-formyl-3-hydroxyphenoxy)methylbenzoate;
3-(2-formyl-3-hydroxyphenoxy)methylbenzoic acid;
benzyl 5-(2-formyl-3-hydroxyphenoxy)pentanoate;
5-[4-(2-formyl-3-hydroxyphenoxy)-N-butyl]tetrazole;
7-(2-formyl-3-hydroxyphenoxy)heptanoic acid;
5-(2-formyl-3-hydroxy-4-n-propoxyphenoxy)pentanoic acid;
5-(4,6-dichloro-2-formyl-3-hydroxyphenoxy)pentanoic acid;

5-(2-formyl-3-hydroxyphenoxy)-N-methylsulphonylpentanamide;
ethyl 4-(2-formyl-3-hydroxyphenoxymethyl)benzoate;
5-(4-chloro-2-formyl-3-hydroxyphenoxy)pentanoic acid;
5-(3-acetylamino-2-formylphenoxy)pentanoic acid;
Aminoguanidine;
4-(2-formyl-3-hydroxyphenoxy)butanoic acid;
6-(2-formyl-3-hydroxyphenoxy)hexanoic acid;
ethyl 4-(3-acetylaminio-2-formylphenoxymethyl)benzoate;
4-(3-acetylamino-2-formylphenoxymethyl)benzoic acid;
2-(2-formyl-3-hydroxyphenoxymethyl)benzoic acid;
5-[4-(2-formyl-3-hydroxyphenoxymethyl)phenyl]tetrazole;
5-(2-formyl-3-hydroxy-4-methoxyphenoxy)pentanoic acid;
3-(2-formyl-3-hydroxyphenoxy)propionitrile;
4-Hydroxyphenylacetaldehyde;
Phenylacetaldehyde;
4-Methoxyphenylacetaldehyde;
1-hydroxy-2-phenylpropane;
3-Phenylproponionaldeyde;
4-Nitrobenzaldehyde;
Methyl 4-formylbenzoate;
4-Chlorobenzaldehyde;
4-Methyloxybenzaldehyde;
4-Methylbenzaldehyde;
8,10-Dioxoundecanoic acid;
4,6-Dioxoheptanoic acid;
Pentanedione;
5-methoxy-1-tetralone;
6-methoxy-1-tetralone;
7-methoxy-1-tetralone;
2-tetralone;
3-hydroxy-1-(4-methoxyphenyl)-3-methyl-2-butanone;
2',4'-dihydroxy-2-(4-methoxyphenyl)acetophenone;
2-hydroxy-1-(4-methyoxyphenyl)-pent-2ene-4one;
Naringenin 4',5,6-trihydroxyflavonone;
4'-methoxy-2-(4-methoxyphenyl)acetophenone;
6,7-dihydroxycoumarin;
7-methoxy-2-tetralone;
6,7-dimethoxy-2-tetralone;
6-hydroxy-4-methylcoumarin;
Homogentisic acid gamma lactone;
6-hydroxy-1,2-naphthoquinone;
8-methoxy-2-tetralone;

and physiologically acceptable salts thereof, where appropriate.

Preferably the compound is 4-(2-formyl-3-hydroxyphenoxymethyl) benzoic acid.

According to a further embodiment of the present invention there is provided use of a compound in the manufacture of a medicament, wherein administration of the compound to a mammal enhances both humoral and cellular responses initiated by an antigenic peptide associated with a disease state, the peptide being expressed as a result of administration to said mammal of a DNA sequence encoding for the peptide;

wherein said compound is selected from:
4-(2-formyl-3-hydroxyphenoxymethyl)benzoic acid;
5-(2-formyl-3-hydroxyphenoxy)pentanamide;
N,N-diethyl 5-(2-formyl-3-hydroxyphenoxy)pentanamide;
N-isopropyl 5-(2-formyl-3-hydroxyphenoxy)pentanamide;
ethyl 5-(2-formyl-3-hydroxyphenoxy)pentanoate;
5-(2-formyl-3-hydroxyphenoxy)pentanonitrile;
(±)-5-(2-formyl-3-hydroxyphenoxy)-2-methylpentanoic acid;
5-(2-formyl-3-hydroxyphenoxy)-2,2-dimethylpentanoic acid;
methyl 3-(2-formyl-3-hydroxyphenoxy)methylbenzoate;
3-(2-formyl-3-hydroxyphenoxy)methylbenzoic acid;
benzyl 5-(2-formyl-3-hydroxyphenoxy)pentanoate;
5-[4-(2-formyl-3-hydroxyphenoxy)-N-butyl]tetrazole;
7-(2-formyl-3-hydroxyphenoxy)heptanoic acid;
5-(2-formyl-3-hydroxy-4-n-propoxyphenoxy)pentanoic acid;
5-(4,6-dichloro-2-formyl-3-hydroxyphenoxy)pentanoic acid;
5-(2-formyl-3-hydroxyphenoxy)-N-methylsulphonylpentanamide;
ethyl 4-(2-formyl-3-hydroxyphenoxymethyl)benzoate;
5-(4-chloro-2-formyl-3-hydroxyphenoxy)pentanoic acid;
5-(3-acetylamino-2-formylphenoxy)pentanoic acid;
Aminoguanidine;
4-(2-formyl-3-hydroxyphenoxy)butanoic acid;
6-(2-formyl-3-hydroxyphenoxy)hexanoic acid;
ethyl 4-(3-acetylaminio-2-formylphenoxymethyl)benzoate;
4-(3-acetylamino-2-formylphenoxymethyl)benzoic acid;
2-(2-formyl-3-hydroxyphenoxymethyl)benzoic acid;
5-[4-(2-formyl-3-hydroxyphenoxymethyl)phenyl]tetrazole;
5-(2-formyl-3-hydroxy-4-methoxyphenoxy)pentanoic acid;
3-(2-formyl-3-hydroxyphenoxy)propionitrile;
4-Hydroxyphenylacetaldehyde;
Phenylacetaldehyde;
4-Methoxyphenylacetaldehyde;
1-hydroxy-2-phenylpropane;
3-Phenylproponionaldeyde;
4-Nitrobenzaldehyde;
Methyl 4-formylbenzoate;
4-Chlorobenzaldehyde;
4-Methyloxybenzaldehyde;
4-Methylbenzaldehyde;
8,10-Dioxoundecanoic acid;
4,6-Dioxoheptanoic acid;
Pentanedione;
5-methoxy-1-tetralone;
6-methoxy-1-tetralone;
7-methoxy-1-tetralone;
2-tetralone;
3-hydroxy-1-(4-methoxyphenyl)-3-methyl-2-butanone;
2',4'-dihydroxy-2-(4-methoxyphenyl)acetophenone;
2-hydroxy-1-(4-methyoxyphenyl)-pent-2ene-4one;
Naringenin 4',5,6-trihydroxyflavonone;
4'-methoxy-2-(4-methoxyphenyl)acetophenone;
6,7-dihydroxycoumarin;
7-methoxy-2-tetralone;
6,7-dimethoxy-2-tetralone;
6-hydroxy-4-methylcoumarin;
Homogentisic acid gamma lactone;
6-hydroxy-1,2-naphthoquinone;
8-methoxy-2-tetralone;

and physiologically acceptable salts thereof, where appropriate.

Preferably the compound is 4-(2-formyl-3-hydroxyphenoxymethyl)benzoic acid and it is preferably administered at a dose of between about 0.1 mg/kg and about 100 mg/kg per administration.

According to a further emobodiment of the invention there is provided a combination of components for separate, sequential or concomitant administration in a method as outlined above, comprising the nucleotide sequence encoding an antigenic peptide and the compound which enhances both cellular and humoral immune responses initiated by the antigenic peptide.

Proliferation of lymph node T cells in response to Ova peptide in vitro (in presence of 0.5% mouse serum). Results show T cell response for ovalbumin in PBS (no adjuvant) and PBS alone, Complete Freunds Adjuvant (CFA) alone and combined with Ova peptide, Bacterial Lipopolysaccharide (LPS) alone and combined with Ova peptide and *Bacillus Calmette Geurin* (HK-BCG) alone and combined with Ova peptide.

FIG. 2.

Proliferation of lymph node T cells in response to pDNA or DNA encoding ovalbumin (PVAC1.Ova) in isolation and in combination with adjuvants LPS, CFA, GM-CSF and Heat-Killed *Listeria monocytogenes* (HKLM).

FIG. 3.

Effects of tucaresol on the specific antibody response to mycobacterial hsp65 after immunisation with pDNA expressing Mhsp65. Mice were immunised with 20 μg pDNA at two occasions, three weeks apart. Two weeks later they were bled and specific IgG (a), IgG2a (b) and IgG1 (c) anti-recombinant M.hsp65 protein were detected by ELISA. $p^* \geq 0.1$ No significant difference in the specific antibody response. $p^{} \leq 0.05$ for comparison between p3 or p3,T and p3M.65 and between p3M.65 and p3M.65 G or p3M.65, T in (a), between p3 or p3,T and p3M.65 or p3M.65 G in (b), and between p3 and or p3,T and p3M.65Gub (c). $p^{*} \leq 0.003$ for comparison between p3 or p3, T and p3M.65 G or p3M.65,T in (a), for comparison between p3 and or p3,T and p3M.65, t and between p3M.65 and p3M.65, t in (b), and between p3 and or p3, T and p3M.65, T in (c). p and h are significant as compared to p3 and p3M.65 respectively.

FIG. 4.

Effect of tucaresol on the proliferative T cell response. Splenocytes from pDNA immunised mice were cultured in the presence of either S6c-E4 alone or infected with vaccinia expressing EBNA-4 9S6C-VE4) or S6C-gpt control tumor cells alone or infected with vaccinia TK- control vaccinia construct 9S6C-gptV). Stimulation index was calculated as described in the methods section.

FIG. 5.

IFNγ response in pDNA immunised mice and the effect of tucaresol on it. Groups of mice were immunised with p3, E4 or E4, T and splenocytes were stimulated in vitro with tumor S6C-E$, S6C-gpt or nothing for 72h. IFNγ tires were determined by specific ELISA.

FIG. 6.

Cytotoxic T-cell response is markedly enhanced in tucaresol treated mice. Groups of HLA-A2/kb transgenic mice were immunised twice with p3M.65, p3M.65γ or p3M.65, T. Splenocytes were cultured with HLA-A2 biding peptide P$ for 5–6 days and were then used as effectors in conventional $^{51}$Cr release assay. Using Jk-A2 kb as targets pulsed with P4, with an irrelevant peptide (Inf) or with nothing as described in the methods section.

FIG. 7.

Tumour outgrowth inhibition is markedly enhanced in tucaresol treated mice. Groups of ACA mice were immunised three times with p3, E4 or E4,T, and were subsequently challenged with 104 S6C tumour cells. Mice were sacrificed when tumour diameter reached 20 mm.

FIG. 8.

IFNγ production is enhanced in tucaresol treated mice following gene gun immunisation.

Figure 8A:
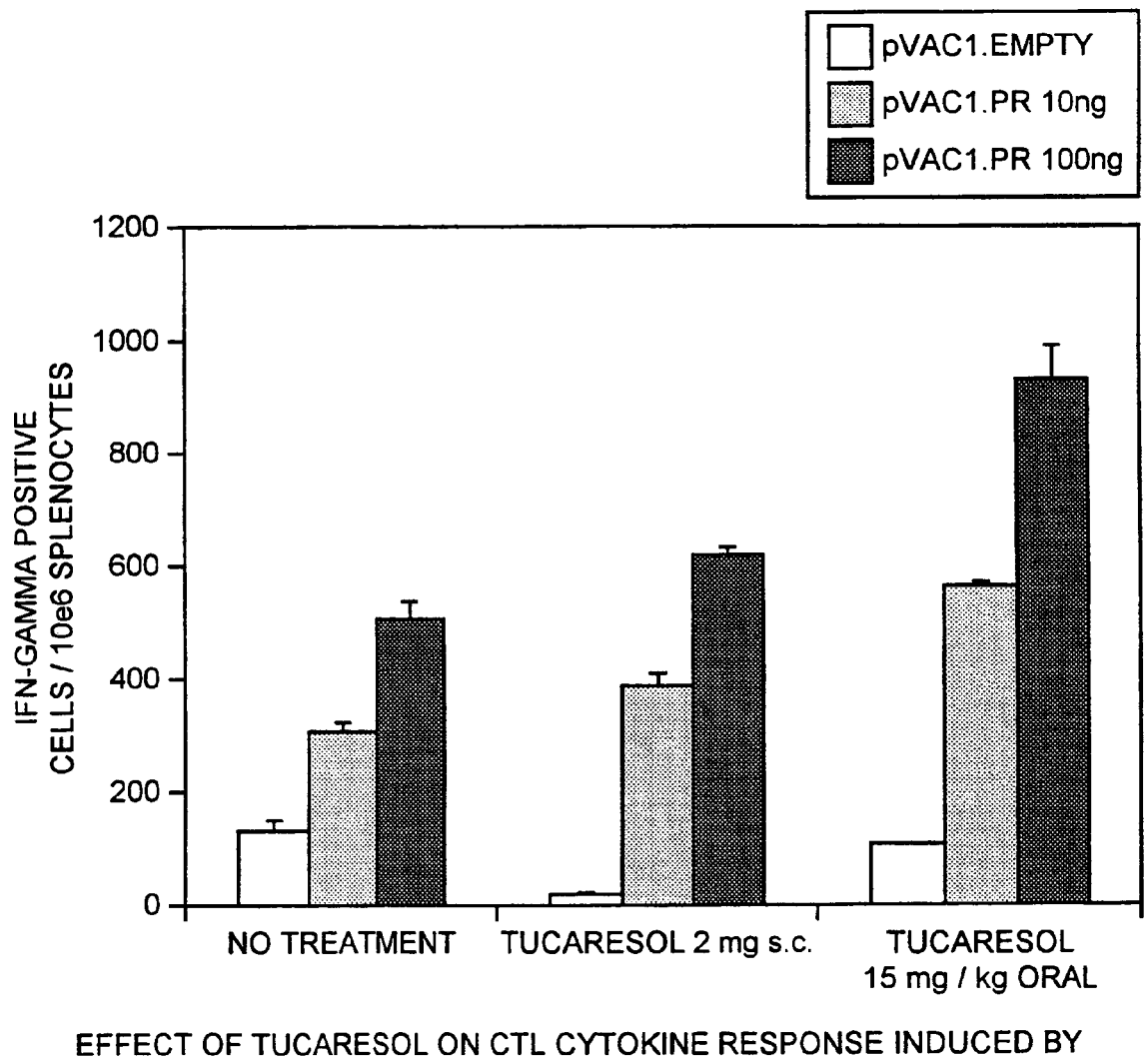

C57BL/6 mice or ACA mice were immunised by gene gun with pVAC1.PR (FIG. 8a) or EBNA-4 (FIG. 8b) respectively either alone or in combination with tucaresol, or the respective negative plasmids. Splenocytes were cultured with a nucleoprotein peptide, or tumour cells expressing the EBNA-4 antigen, or antigen negative tumour cells. IFNγ titres were determined by specific ELISPOT assay (FIG. 8b) or by specific ELISA assay (FIG. 8a).

FIG. 9.

Tucaresol Enhances the lytic CTL response induced by gene gun DNA immunisation.

Figure 9A:
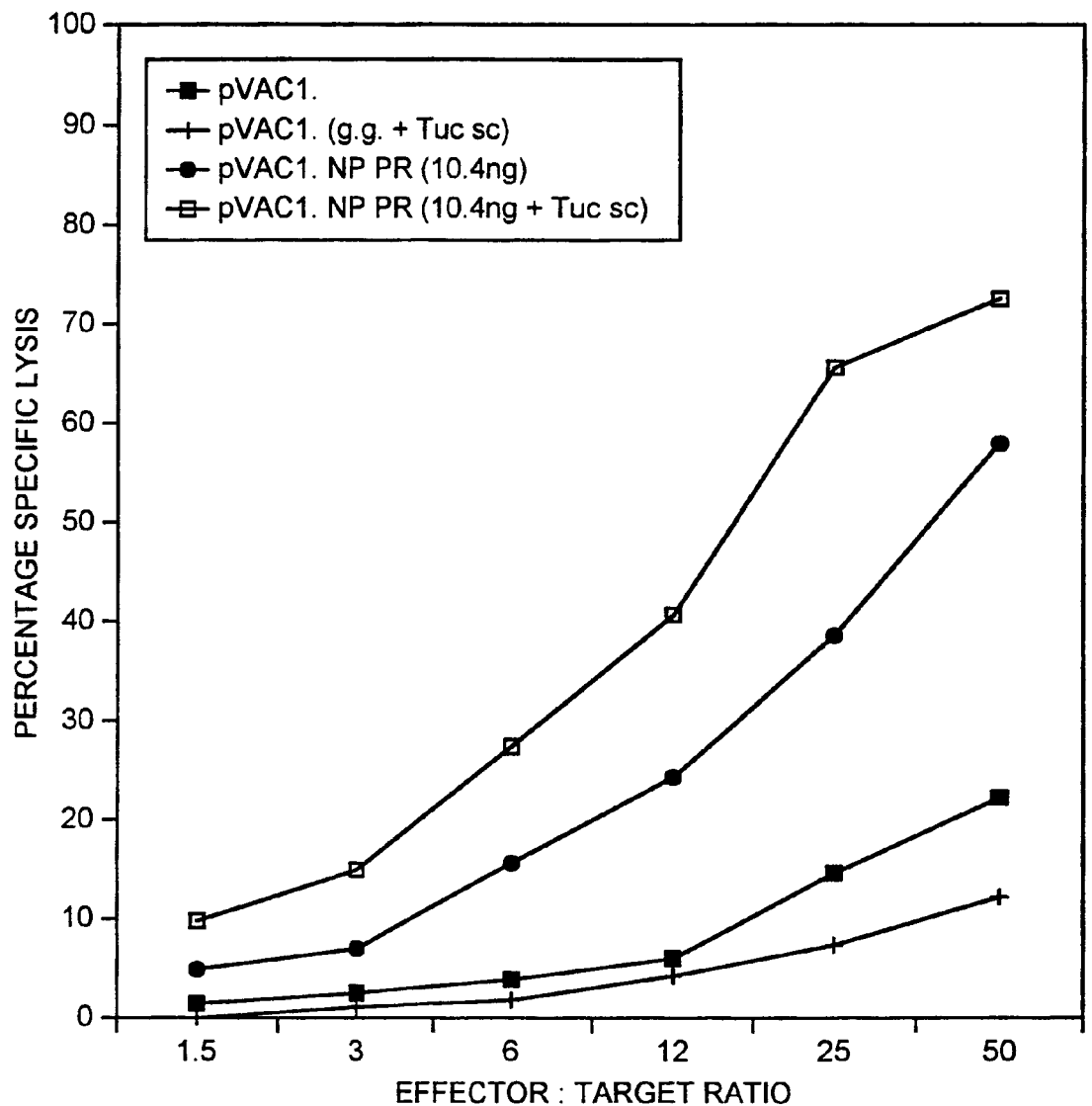
Figure 9B:
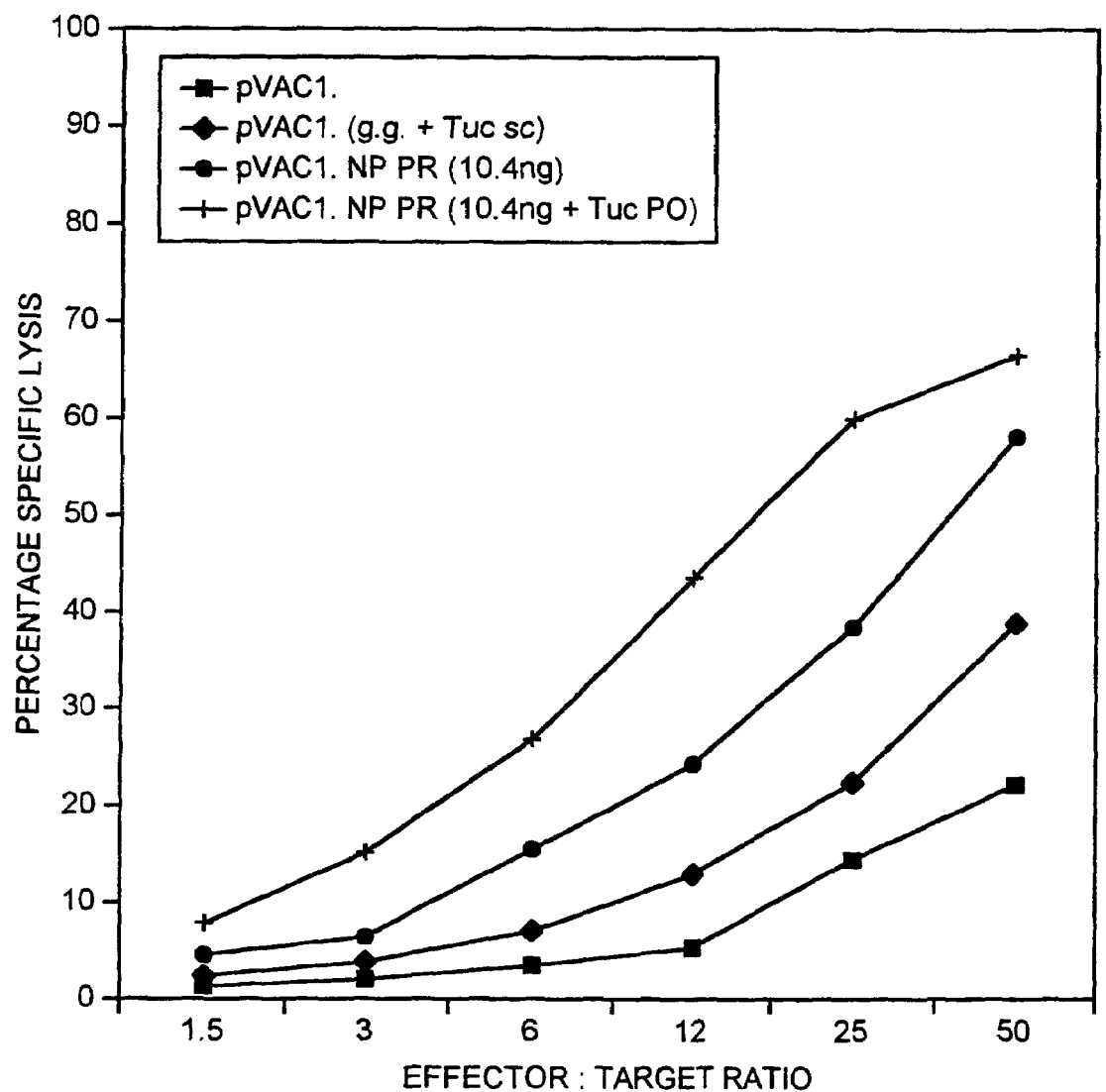

C57B1/6 mice were immunised with plasmid DNA encoding the influenza virus nucleoprotein with or without tucaresol given subcutaneously (FIG. 9a) or orally (FIG. 9b). Splenocytes were restimulated in-vitro with A/PR8/34 virus. Standard europium release techniques were used to determine specific lysis of MHC matched target cells pulsed with H-2 $D^b$-restricted NP peptide.

DETAILED DESCRIPTION OF THE INVENTION

Throughout this specification and the appended claims, unless the context requires otherwise, the words "comprise" and "include" or variations such as "comprising", "comprises", "including", "includes", etc., are to be construed inclusively, that is, use of these words will imply the possible inclusion of integers or elements not specifically recited.

As described above, the present invention relates to vaccination methods, and in particular to improvements of methods of vaccination involving the introduction into a mammal of DNA which encodes for an antigenic protein or peptide, such that the protein or peptide will be expressed within the mammalian body to thereby induce an immune response within the mammal, against the antigenic protein or peptide. Such techniques are well known and are fully described in (1) as referred to above.

It is possible for the vaccination methods according to the present application to be adapted for protection of mammals against a variety of disease states such as, for example, viral, bacterial or parasitic infections, cancer, allergies and autoimmune disorders. Some specific examples of disorders or disease states which can be protected against or treated by using the methods or compositions according to the present invention, are as follows:

Viral Infections

Hepatitis viruses A, B, C, D & E, HIV, herpes viruses 1, 2, 6 & 7, -cytomegalovirus, varicella zoster, papilloma virus, Epstein Barr virus, influenza viruses, para-influenza viruses, adenoviruses, coxsakie viruses, picorna viruses, rotaviruses, respiratory syncytial viruses, pox viruses, rhinoviruses, rubella virus, papovirus, mumps virus, measles virus.

Bacterial Infections

Mycobacteria causing TB and leprosy, pneumocci, aerobic gram negative bacilli, mycoplasma, staphyloccocal infections, streptococcal infections, *salmonellae, chlamydiae*.

Parasitic

Malaria, leishmaniasis, trypanosomiasis, toxoplasmosis, schistosomiasis, filariasis, Cancer Breast cancer, colon cancer, rectal cancer, cancer of the head and neck, renal cancer, malignant melanoma, laryngeal cancer, ovarian cancer, cervical cancer, prostate cancer.

Allergies

Rhinitis due to House dust mite, pollen and other environmental allergens

Autoimmune disease

Systemic lupus erythematosis

It is to be recognised that these specific disease states have been referred to by way of example only, and are not intended to be limiting upon the scope of the present invention.

The DNA sequences referred to in this application, which are to be expressed within a mammalian system, in order to induce an antigenic response, may encode for an entire protein, or merely a shorter peptide sequence which is capable of initiating an antigenic response. Throughout this specification and the appended claims, the phrase "antigenic peptide" is intended to encompass all peptide or protein sequences which are capable of inducing an immune response within the animal concerned. Most preferably, however, the DNA sequence will encode for a full protein which is associated with the disease state, as the expression of full proteins within the animal system are more likely to mimic natural antigen presentation, and thereby evoke a full immune response. Some non-limiting examples of known antigenic peptides in relation to specific disease states include the following:

HBV—PreS1 PreS2 and Surface env proteins, core and pol

HIV—gp120 gp40, gp160, p24, gag, pol, env, vif, vpr, vpu, tat, rev, nef

Papilloma—E1, E2, E3, E4, E5, E6, E7, E8, L1, L2

HSV—gL, gH, gM, gB, gC, gK, gE, gD, ICP47, ICP36, ICP4

Influenza—haemagglutin, nucleoprotein

TB—Mycobacterial super oxide dismutase, 85A, 85B, MPT44, MPT59, MPT45, HSP10, HSP65, HSP70, HSP90, PPD 19 kDa Ag, PPD 38 kDa Ag.

In order to obtain expression of the antigenic peptide within mammalian cells, it is necessary for the DNA sequence encoding the antigenic peptide to be presented in an appropriate vector system. For example, the vector selected may comprise a bacterial plasmid and a strong viral promoter and polyadenylation/transcriptional termination sequence arranged in the correct order to obtain expression of the antigenic peptides. The construction of vectors which include these components and optionally other components such as enhancers, restriction enzyme sites and selection genes, such as antibiotic resistance genes, is well known to persons skilled in the art and is explained in detail in Maniatis et al (21).

As it is important to prevent the plasmids replicating within the mammalian host and integrating within the chromosomal DNA of the animal, the plasmid will preferably be produced without an original of replication that is functional in eukaryotic cells.

The methods and compositions according to the present invention can be used in relation to prophylactic or treatment procedures of all mammals including, for example, domestic animals, laboratory animals, farm animals, captive wild animals and most preferably, humans.

The compounds recited above which have been identified by the present inventors as exhibiting the favourable activity of enhancing both humoral and cellular immunogenic activity initiated by DNA vaccine administration are known compounds, previously reported in WO94/07479 as having immunopotentiatory properties. In particular, the preferred compound 4-(2-formol-3-hydroxyphenoxymethyl)benzoic acid, which is also known as tucaresol, was originally described in EP 0054924 and has been reported as having immunopotentiatory activity and as being useful for treatment of various disorders including HIV, HBV, HCV, tumours and sickle cell anaemia. It is thought that the reported activity of tucaresol can be explained by its ability to form Schiff bases and that it can thereby substitute for physiological donors or carbonyl groups and provide a co-stimulatory signal to CD4 Th-cells. It was previously reported that tucaresol enhanced CD4 Th-cell response, selectively favouring a Th 1-type profile over Th 2 (22), whereas the present inventors have demonstrated that it is capable of enhancing both Th 1 and Th 2 isotypes of antibody in a murine model.

By referring to enhancement of both humoral and cellular immune responses initiated by the antigenic peptide, and caused by the compounds of the present invention, it is intended to convey that both serum antibody levels and cytotoxic T lymphocyte (CTL) levels respectively will be raised as a result of administration of the compounds, compared to levels associated with administration of DNA sequence encoding for the antigenic peptide alone. Such levels can be quantified by methods well known in the art, as will be further explained in the appended examples.

The vectors which comprise the DNA sequences encoding antigenic peptides can be administered in a variety of manners. It is possible for the vectors to be administered in a naked form (that is as naked DNA not in association with liposomal formulations, with viral vectors or transfection facilitating proteins) suspended in an appropriate medium, for example a buffered saline solution such as PBS and then injected intramuscularly, subcutaneously, intraperitonally or intravenously, although some earlier data suggests that intramuscular or subcutaneous injection is preferable (23), (the disclosure of which is included herein in its entirety by way of reference). It is additionally possible for the vectors to be encapsulated by, for example, liposomes or within polylactide co-glycolide (PLG) particles (25) for administration via the oral, nasal or pulmonary routes. It is also possible, according to a preferred embodiment of the invention, for intradermal administration of the vector, preferably via use of gene-gun (particularly particle bombardment) administration techniques. Such techniques may involve lyophilisation of a suspension comprising the vector and subsequent coating of the vector on to gold beads which are then administered under high pressure into the epidermis, such as, for example, as described in (26). The amount of DNA delivered will vary significantly, depending upon the species and weight of mammal being immunised, the nature of the disease state being treated/protected against, the vaccination protocol adopted (i.e. single administration versus repeated doses), the route of administration and the potency and dose of the adjuvant compound chosen. Based upon these variables, a medical or veterinary practitioner will readily be able to determine the appropriate dosage level.

It is possible for the DNA vector, including the DNA sequence encoding the antigenic peptide, to be administered on a once off basis or to be administered repeatedly, for example, between 1 and 7 times, preferably between 1 and 4 times, at intervals between about 1 day and about 18 months. Once again, however, this treatment regime will be significantly varied depending upon the size and species of animal concerned, the disease which is being treated/protected against, the amount of DNA administered, the route of administration, the potency and dose of adjuvant compound selected and other factors which would be apparent to a skilled veterinary or medical practitioner.

The adjuvant compound specified herein can similarly be administered via a variety of different administration routes, such as for example, via the oral, nasal, pulmonary, intramuscular, subcutaneous, intradermal or topical routes. This administration may take place between about 14 days prior to and about 14 days post administration of the DNA sequence, preferably between about 7 days prior to and about 7 days post administration of the DNA sequence, more preferably between about 24 hours prior to and 24 hours post administration of the DNA sequence, and particularly preferably, substantially simultaneous with administration of the DNA sequence. By "substantially simultaneous" what is meant is that administration of the compound is preferably at the same time as administration of the DNA sequence, or if not, at least within a few hours either side of DNA sequence administration. In the most preferred treatment protocol, the compound will be administered substantially simultaneously to administration of the DNA sequence, and then again on approximately a daily basis for up to 14 days post DNA sequence administration, preferably daily for the 3 days following initial administration. Obviously, this protocol can be varied as necessary, in accordance with the type of variables referred to above. Once again, depending upon such variables, the dose of administration will also vary, but may, for example, range between about 0.1 mg per kg to about 100 mg per kg, where "per kg" refers to the body weight of the mammal concerned. This administration of the adjuvant compound would preferably be repeated with each subsequent or booster administration of the DNA sequence. Most preferably, the administration dose will be between about 0.1 mg per kg to about 10 mg per kg, preferably between about 1 mg per kg and about 5 mg per kg.

While it is possible for the adjuvant compounds to be administered in the raw chemical state, it is preferable for administration in the form of a pharmaceutical composition. That is, the compounds will preferably be combined with one or more pharmaceutically or veterinarily acceptable carriers, and optionally other therapeutic ingredients. The carrier(s) must be "acceptable" in the sense of being compatible with other ingredients within the formulation, and not deleterious to the recipient thereof. The nature of the formulations will naturally vary according to the intended administration route, and may be prepared by methods well known in the pharmaceutical art. All methods include the step of bringing into association a compound of the invention (the adjuvant compound) with an appropriate carrier or carriers. In general, the formulations are prepared by uniformly and intimately bringing into association the compound with liquid carriers or finely divided solid carriers, or both, and then, if necessary, shaping the product into the desired formulation. Formulations of the present invention suitable for oral administration may be presented as discrete units such as capsules, cachets or tablets each containing a pre-determined amount of the active ingredient; as a powder or granules; as a solution or a suspension in an aqueous liquid or a non-aqueous liquid; or as an oil-in-water liquid emulsion or a water-in-oil emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent.

The tablets may optionally be coated or scored and may be formulated so as to provide slow or controlled release of the active ingredient.

Formulations for injection via, for example, the intramuscular, intraperitonile, or subcutaneous administration routes include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilised) condition requiring only the addition of the sterile liquid carrier, for example, water for injections, immediately prior to use. Extemporaneous injection solutions and suspensions may be prepared from sterile powders, granules and tablets of the kind previously described. Formulations suitable for pulmonary administration via the buccal or nasal cavity are presented such that particles containing the active ingredient, desirably having a diameter in the range of 0.5 to 7 microns, are delivered into the bronchial tree of the recipient. Possibilities for such formulations are that they are in the form of finely comminuted powders which may conveniently be presented either in a piercable capsule, suitably of, for example, gelatine, for use in an inhalation device, or alternatively, as a self-propelling formulation comprising active ingredient, a suitable liquid propellant and optionally, other ingredients such as surfactant and/or a solid diluent. Self-propelling formulations may also be employed wherein the active ingredient is dispensed in the form of droplets of a solution or suspension. Such self-propelling formulations are analogous to those known in the art and may be prepared by established procedures. They are suitably provided with either a manually-operable or automatically functioning valve having the desired spray characteristics; advantageously the valve is of a metered type delivering a fixed volume, for example, 50 to 100 μL, upon each operation thereof.

In a further possibility, the active ingredient may be in the form of a solution for use in an atomiser or nebuliser whereby an accelerated airstream or ultrasonic agitation is employed to produce a find droplet mist for inhalation.

Formulations suitable for intranasal administration generally include presentations similar to those described above for pulmonary administration, although it is preferred for such formulations to have a particle diameter in the range of about 10 to about 200 microns, to enable retention within the nasal cavity. This may be achieved by, as appropriate, use of a powder of a suitable particle size, or choice of an appropriate valve. Other suitable formulations include coarse powders having a particle diameter in the range of about 20 to about 500 microns, for administration by rapid inhalation through the nasal passage from a container held close up to the nose, and nasal drops comprising about 0.2 to 5% w/w of the active ingredient in aqueous or oily solutions.

Examples of appropriate formulations which comprise the adjuvant compounds according to the present invention are provided within WO94/07479, the disclosure of which is included herein by reference, in its entirety.

In a preferred embodiment of the invention, it is possible for the vector which comprises the DNA sequence encoding the antigenic peptide to be administered within the same formulation as the adjuvant compound. In a particularly preferred embodiment the adjuvant compound is prepared in a form suitable for gene-gun administration, and is administrated via that route substantially simultaneous to administration of the DNA sequence. For preparation of formulations suitable for use in this manner, it may be necessary for the adjuvant compound to be lyophilised and adhered onto, for example, gold beads which are suited for gene-gun administration.

Even if not formulated together, it may be appropriate for the adjuvant compounds to be administered at or about the same administration site as the DNA sequence.

Other details of pharmaceutical preparations can be found in (24), the disclosure of which is included herein in its entirety, by way of reference.

The present invention will now be described further, with reference to the following non-limiting examples:

EXAMPLE 1

Activity in Conventional Adjuvants in DNA Vaccination Compared to Peptide Immunisation Lymphoid cells from TCR-transgenic mice, expressing a receptor specific for an ovalbumin antigen were transferred into normal syngeneic mice. These mice were then immunised subcutaneously with ovalbumin peptide with or without adjuvants. Three days later, regional lymph node cells were removed and their proliferative response to ovalbumin peptide was measured by means of incorporation of tritiated thymidine into DNA. This provides a measure of the degree of specific T-cell priming that occurred in vivo in response to immunisation. Immunisation with ovalbumin peptide alone (○) resulted in a significant but low level of T-cell priming compared with mock immunisation (●). Bacterial lipopolysaccharide (LPS) (⊗), complete Freunds adjuvant (CFA) (□), and *Bacillus* Calmette Geurin (HK-BCG) (⊕), all provided significant enhancement of this response. In the absence of an immunising antigen, administration of bacterial lipopolysaccharide (LPS) (▲), complete Freunds adjuvant (CFA) (■), and *Bacillus* Calmette Geurin (HK-BCG) (▼), had minimal effects on subsequent proliferation in response to ova peptide.

Lymphoid cells from TCR-transgenic mice, expressing a receptor specific for an ovalbumin antigen were transferred into normal syngeneic mice. These mice were then immunised subcutaneously (by means of gene gun) with plasmid DNA (pVAC1) or with plasmid DNA construct encoding ovalbumin (pVAC1.Ova) with or without adjuvants given subcutaneously. Three days later, regional lymph node cells were removed and their proliferative response to ovalbumin peptide was measured by means of incorporation of tritiated thymidine into DNA. This provides a measure of the degree of specific T-cell priming that occurred in vivo in response to immunisation. A control group were immunised with ovalbumin peptide in complete Freunds adjuvant which produced substantial T-cell priming (♦). DNA immunisation with pVAC1.Ova (⊗) produced significant T-cell priming compared with immunisation with the empty vector (○). However, in contrast to the conventional peptide immunisation, none of the adjuvants were able to enhance this response to DNA immunisation. LPS (▲), heat-killed *Listeria monocytogenes* (HKLM) (▼), GM-CSF (◇), and complete Freunds adjuvant (CFA) (⊕), all failed to enhance the response to DNA vaccination. [An anomalous high response was seen in with the empty vector control using HKLM as adjuvant].

EXAMPLE 2

Tucaresol Enhances the Production of Antigen Specific Antibodies

The effect of tucaresol on immunisation with a plasmid DNA coding for the mycobacterial heat shock protein 65 (M.hsp65) antigen was analysed, and compared the effect of tucaresol to that of plasmids expressing the cytokines GM-CSF and IFNγ.

Figure 1:
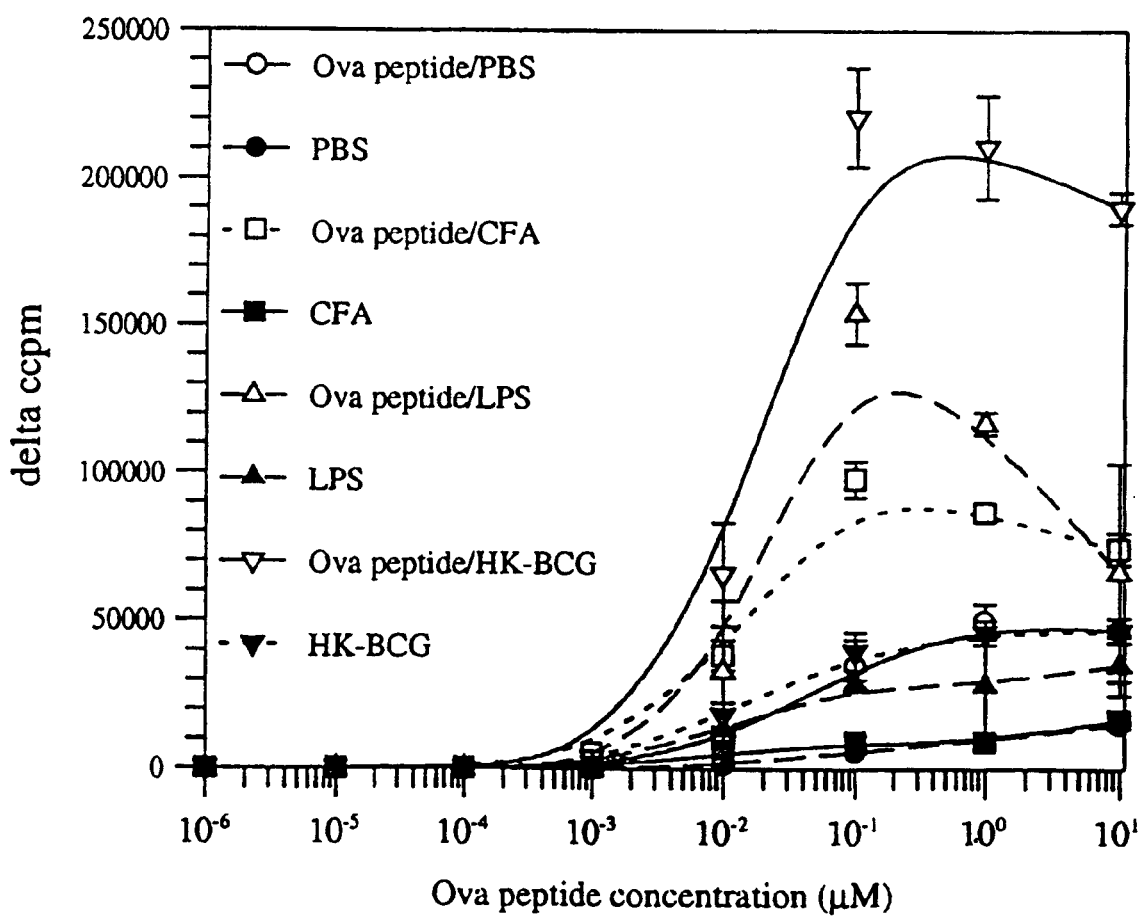
FIG. 1.
Figure 2:
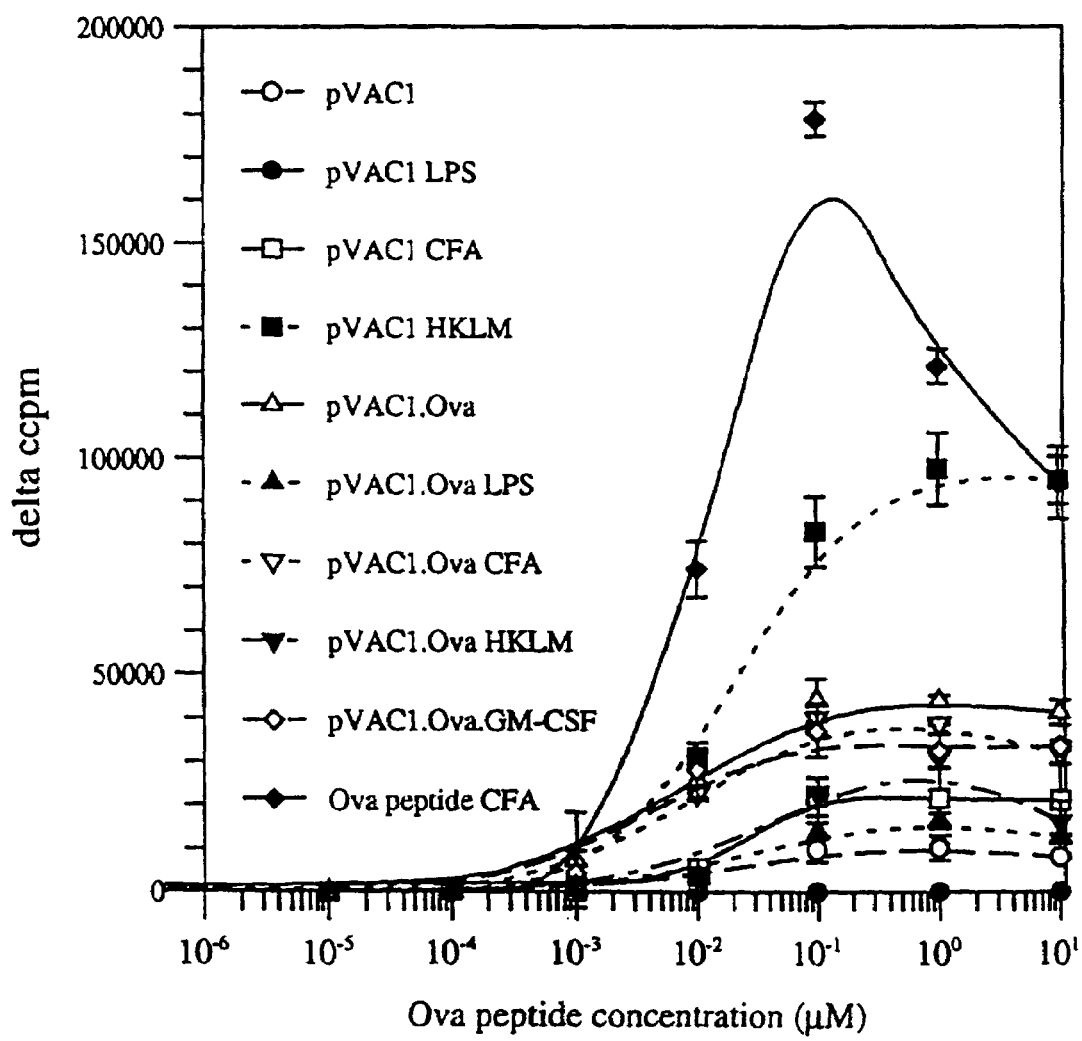
Figure 3A:
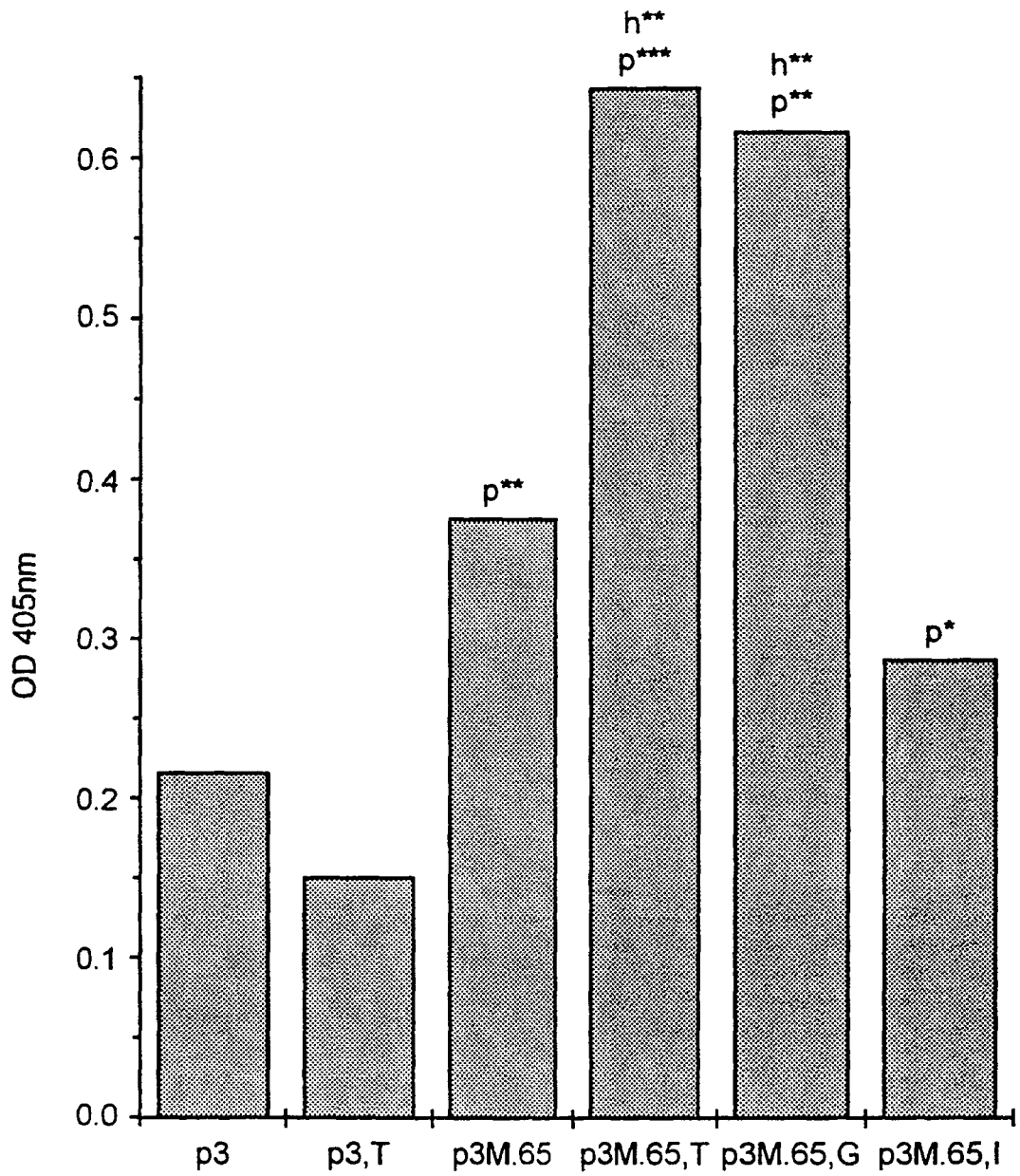

Groups of mice were immunised intramuscularly (i.m.) with 20 μg of a plasmid (p3). Significant amounts of antibodies to M>hsp65 could be detected in sera from p3M.65 immunised mice, but not in the p3 immunised ones (FIG. 3a). The antibody titres were markedly increased when 1 mg of tucaresol was administered subcutaneously simultaneously with the M.hsp plasmid 9p3M.65, T). In contrast, no increase in the specific antibody response was detected in a group of mice immunised with the control plasmid and tucaresol (p3, T), excluding the possibility that a general increase in non-specific cross-reactive antibodies due to the high degree of immuno-potentiation associated with tucaresol administration accounted for the observed effect. (FIG. 3a).

We also compared in the same experiment the effect of tucaresol with that of injecting plasmids expressing the cytokines GM-CSF and IFNγ. The p3M.65 plasmid was administered alone or in equimolar combination with either a GM-CSF expressing plasmid (p3M.65, G), an IFNγ expressing plasmid (p3M.65, γ), or a mixture of GM-CSF and IFNγ expressing plasmids (p3M.65, Gγ). The anti-M.hsp65 titres were markedly increased when the GM-CSF plasmid was included in the immunisation as compared with to p3M65. In contrast to the potentiating effect of the GM-CSF plasmid on the M.hsp65 specific antibody response, there was insignificant antibody response when the IFNγ expressing plasmid was included in line with previously published data. Combining both cytokine plasmids seemed to antagonise the enhancing effect of the GM-CSF plasmid, reducing the response to levels essentially similar to that observed when immunising with p3M.65 only (data not shown). Collectively, these results demonstrate that tucaresol has a potent capacity to enhance the antibody response induced by genetic immunisation with the M.hsp65 antigen, comparable to the effect of the GM-CSF plasmid.

Figure 3B:
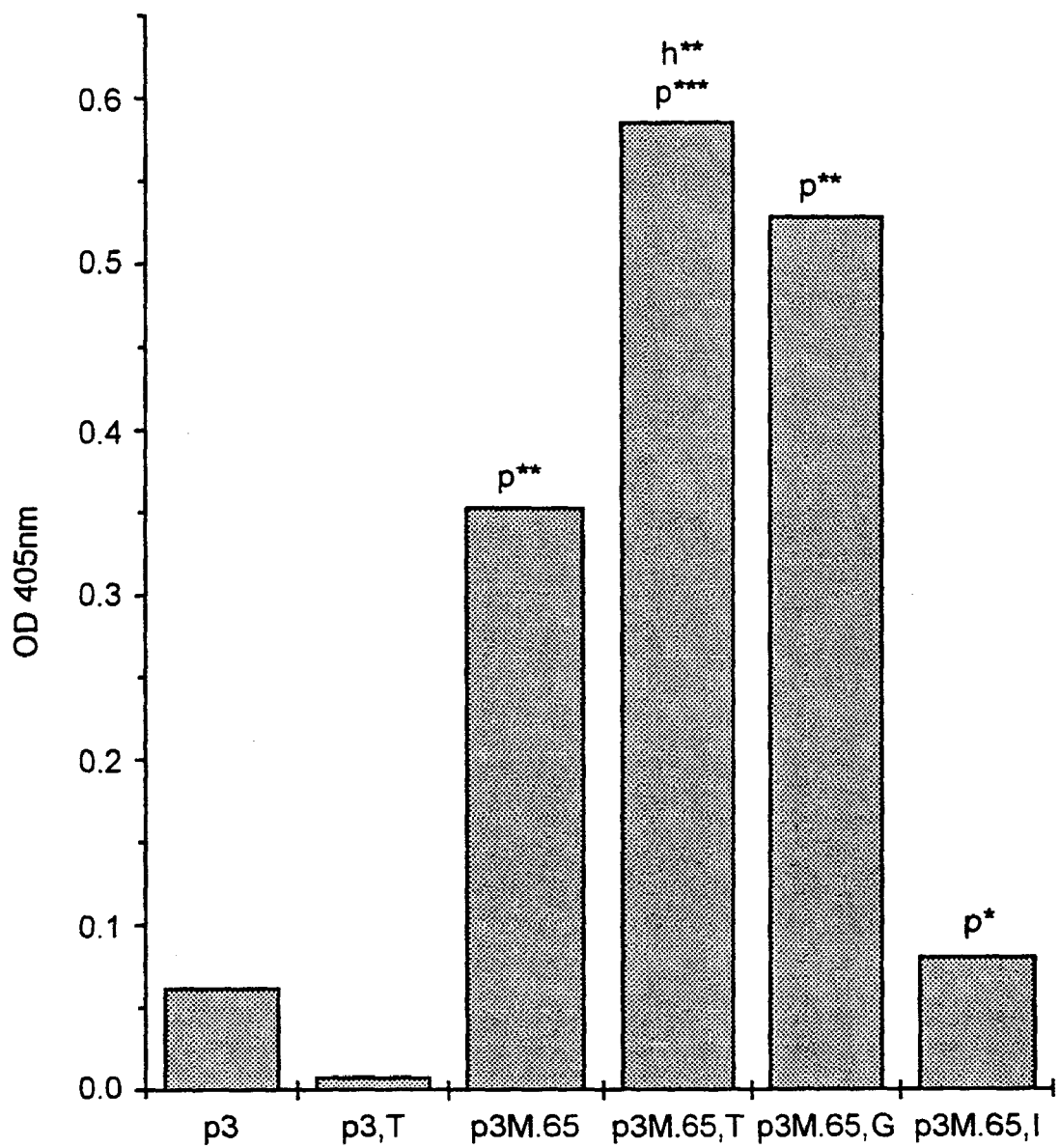

We have analysed the isotype of the anti-M.hsp65 antibodies. p3M.65 immunised mice produced significant amounts of IgG2a anti-M.hsp65 antibodies. This titre was significantly (P=0.003) increased in mice receiving tucaresol (FIG. 3b). This clear enhancement of a Th1 associated antibody response was unique as immunisation with p3M.65,G, p3M.65γ or p3M.65 Gγ could not exert such an effect. The inclusion of the IFNγ expressing plasmid in the immunisation did not enhance the IgG2a anti-M.hsp65 antibody response.

Figure 3C:
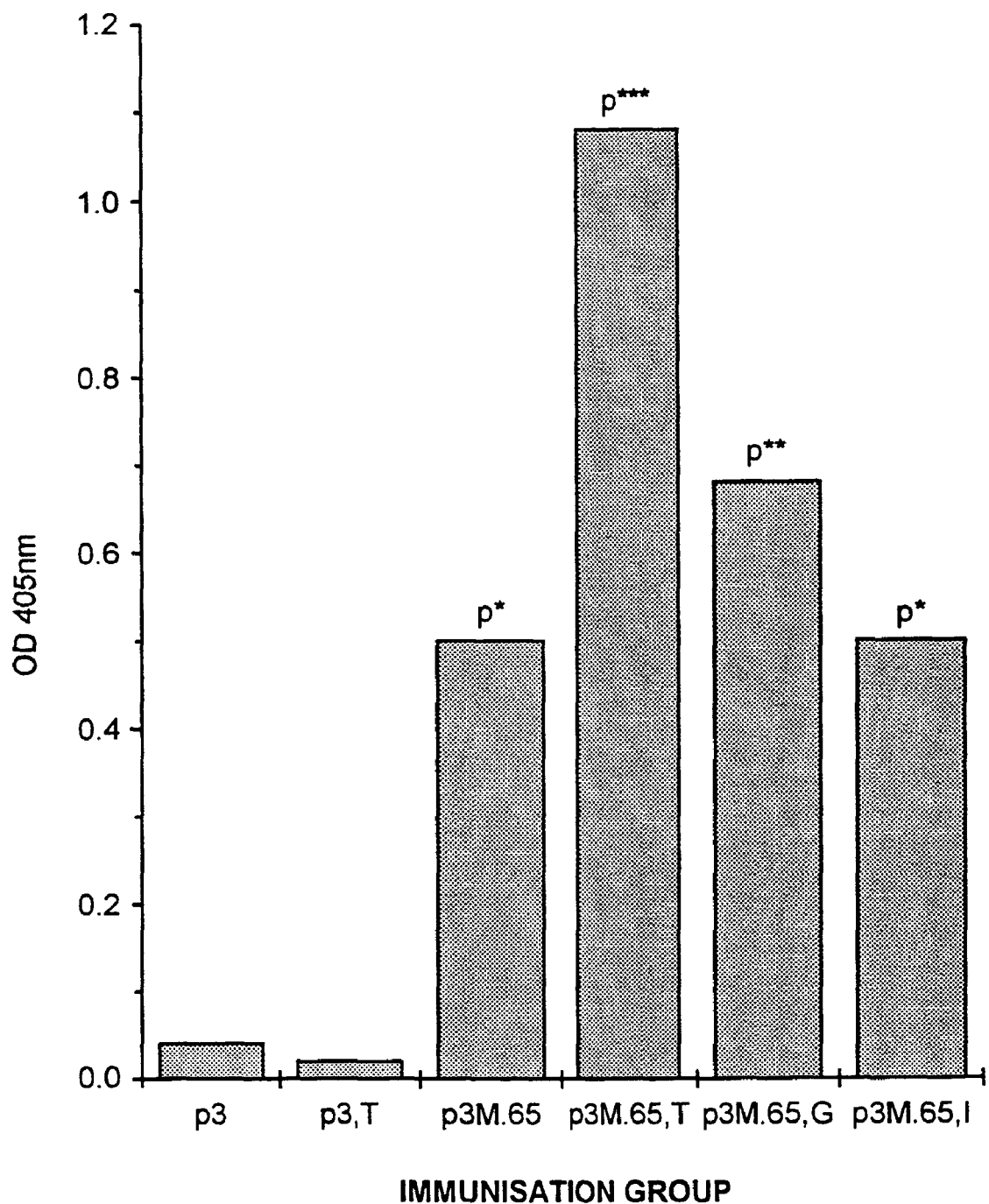

A Th2 associated anti-M.hsp65 IgG1 antibody response could not be detected in a significant amount of mice receiving p3M.65,G, p3M.65γ or p3M.65 Gγ. This response was induced in a significant amount (P=0.003) however, in mice receiving p3M.65, T and to a lesser extent (P=0.027) in pM.65G immunised mice as compared to p3 immunised mice (FIG. 3c).

Taken together, our data prove that a significant increase in the specific antibody response as a result of genetic immunisation could be achieved by the administration of tucaresol. Although this administration strongly enhanced the Th1 associated response, it did also induce a Th2 associated antibody response. This is the first time tucaresol is reported to enhance the production of a specific antibody response.

EXAMPLE 3

Tucaresol Enhances the Specific T-Cell Proliferative Response.

Figure 4:
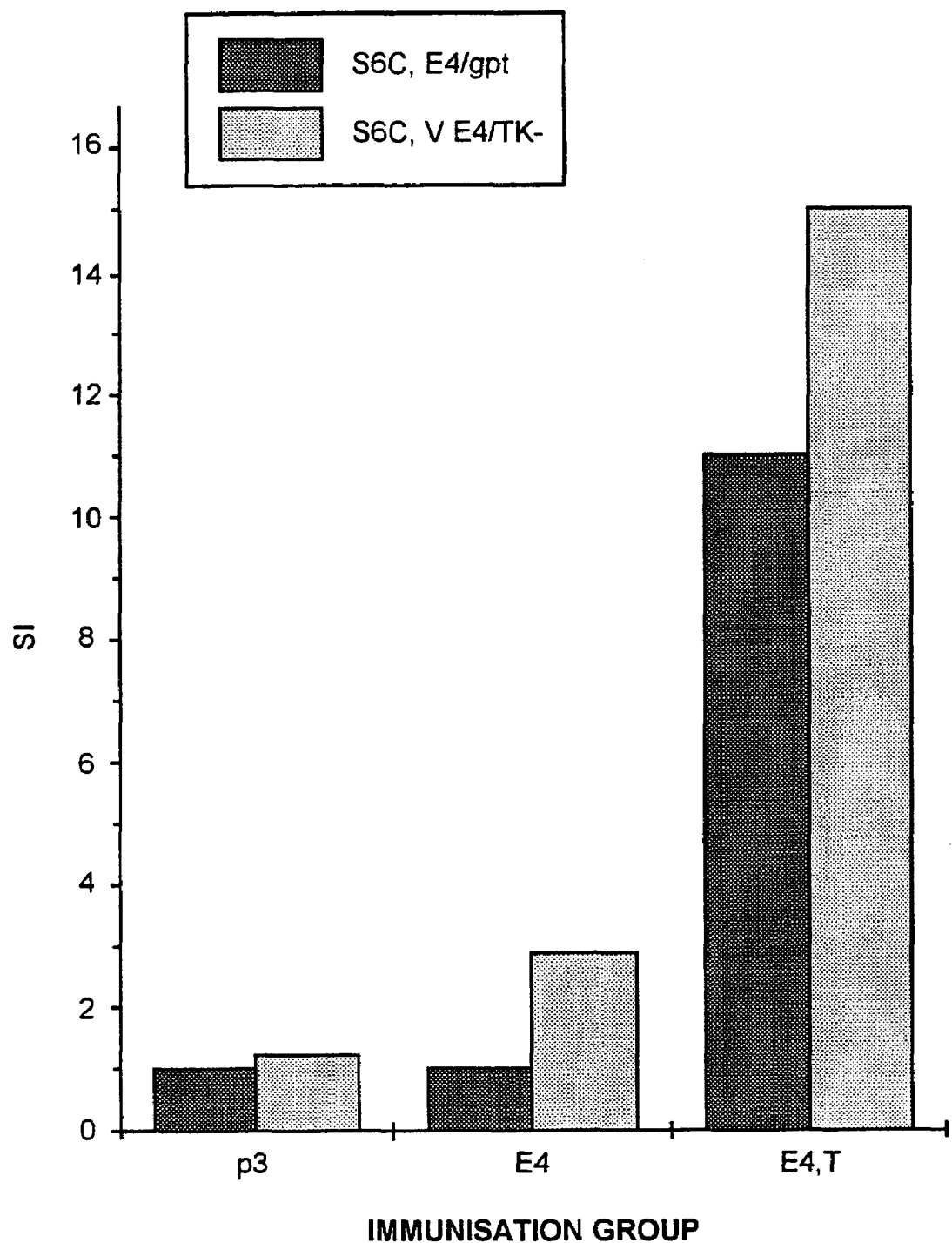
Figure 5:
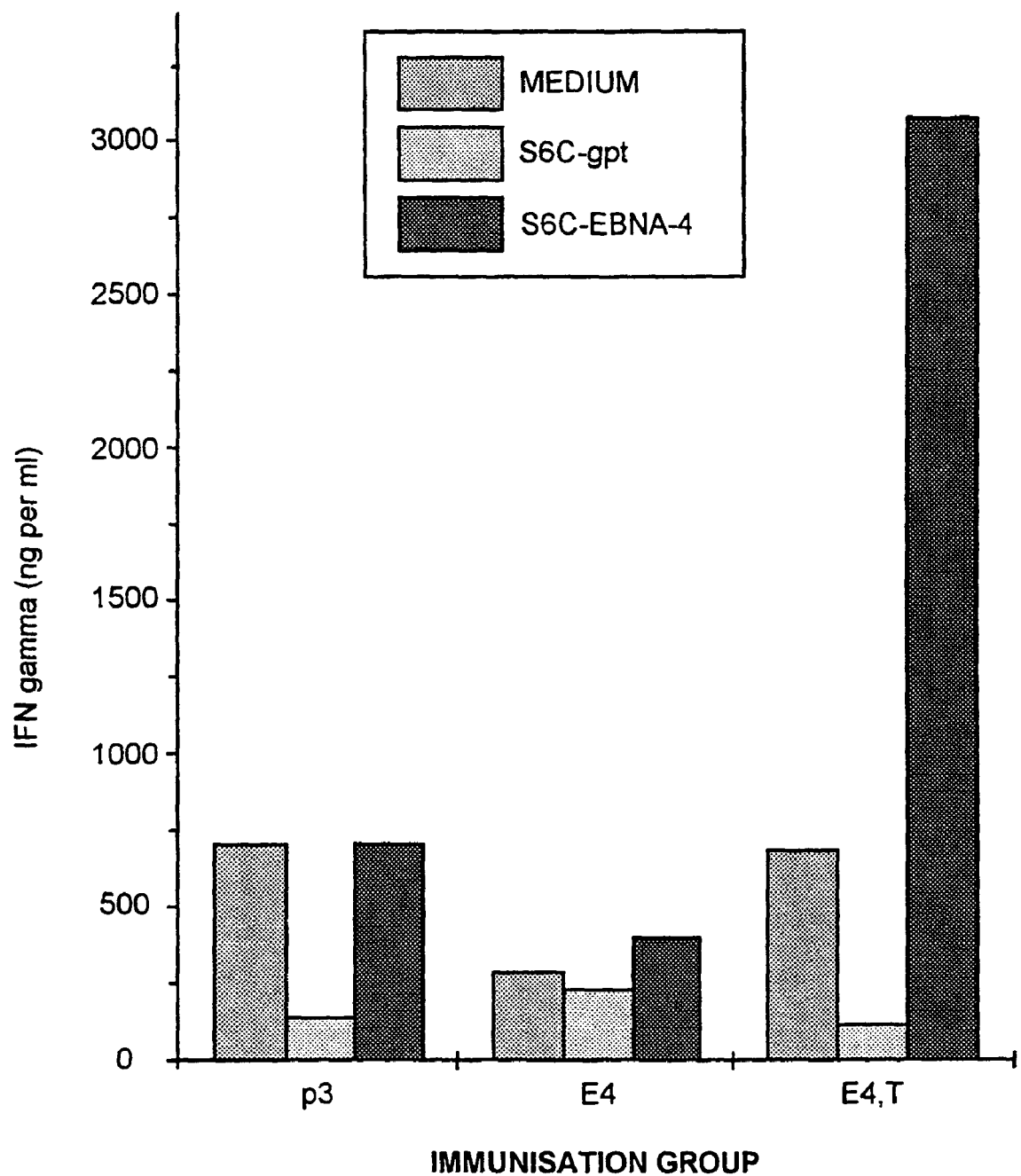

We next analysed the effect of tucaresol on the proliferative T-cell response induced by vaccination with pDNA expressing the Epstein Barr Virus (EBV) nuclear antigen number 4 (EBNA-4). Groups of mice were immunised i.m. with control plasmid p3 or with the EBNA-4 expressing plasmid (E4) or with E4 plus treatment with tucaresol (E4, T). A minimal proliferative response was detected in the splenocyte cultures from E4 immunised mice when stimulated with the syngeneic EBNA-4 transfected carcinoma line (S6C-E4). Interestingly, a much stronger proliferative response to S6C-E4 was obtained with splenocytes from mice immunised i.m. with the E4 and treated s.c. with tucaresol (FIG. 4). EBNA-4 vaccinia infected stimulators (S6C-VE4) also induced a higher proliferative response than S6C-E4 in the splenocytes from both E4 immunised and the E4, T immunised mice as previously reported. Proliferation was calculated as simulation index (SI) using the formula: SI=splenocyte proliferation towards S6C-EBNA-4 transfectant (EBNA-4 vaccinia infected)/splenocyte proliferation towards S6C-gpt (TK-vacccinia infected) control transfectant. Again, this response was antigen focused as there was no detectable proliferation in the splenocytes from control immunised mice (p3) towards S6C-E4 or EBNA-4 vaccinia infected cells above that toward S6C-gpt or control TK-vaccinia infected S6c-gptV respectively (FIG. 4).

EXAMPLE 4

Tucaresol Significantly Enhances the Production of Th-1 Cytokines.

pDNA immunisation is associated with a predominant Th-1 response as characterised by production of Th1 cytokines including IFNγ. To assess the capacity of tucaresol to enhance this Th-1 response, mice were immunised i.m. with p3, E4 or E4 with simultaneous administration of tucaresol s.c. Little, if any IFNγ was produced by splenocytes from mice immunised with E4 only in response to specific stimulation with S6C-E4 as compared to production from control splenocytes from p3 immunised mice or the production in response to S6C-gpt. Interestingly, splenocytes from form mice immunised with e4 and treated with tucaresol produced the highest amounts of IFNγ in response to specific in vitro stimulation with S6C-E4 but did not in response to control stimulation with S6C-gpt. We were unable to detect the Th2 cytokine IL-4 production in response to specific stimulation in splenocytes cultures from any group (data not shown). We therefore conclude that tucaresol administration together with pDNA vaccination is a highly efficient way of promoting a specific Th1 dominated cytokine response.

EXAMPLE 5

Augmentation of the Specific CTL Response by Tucaresol

Figure 6:
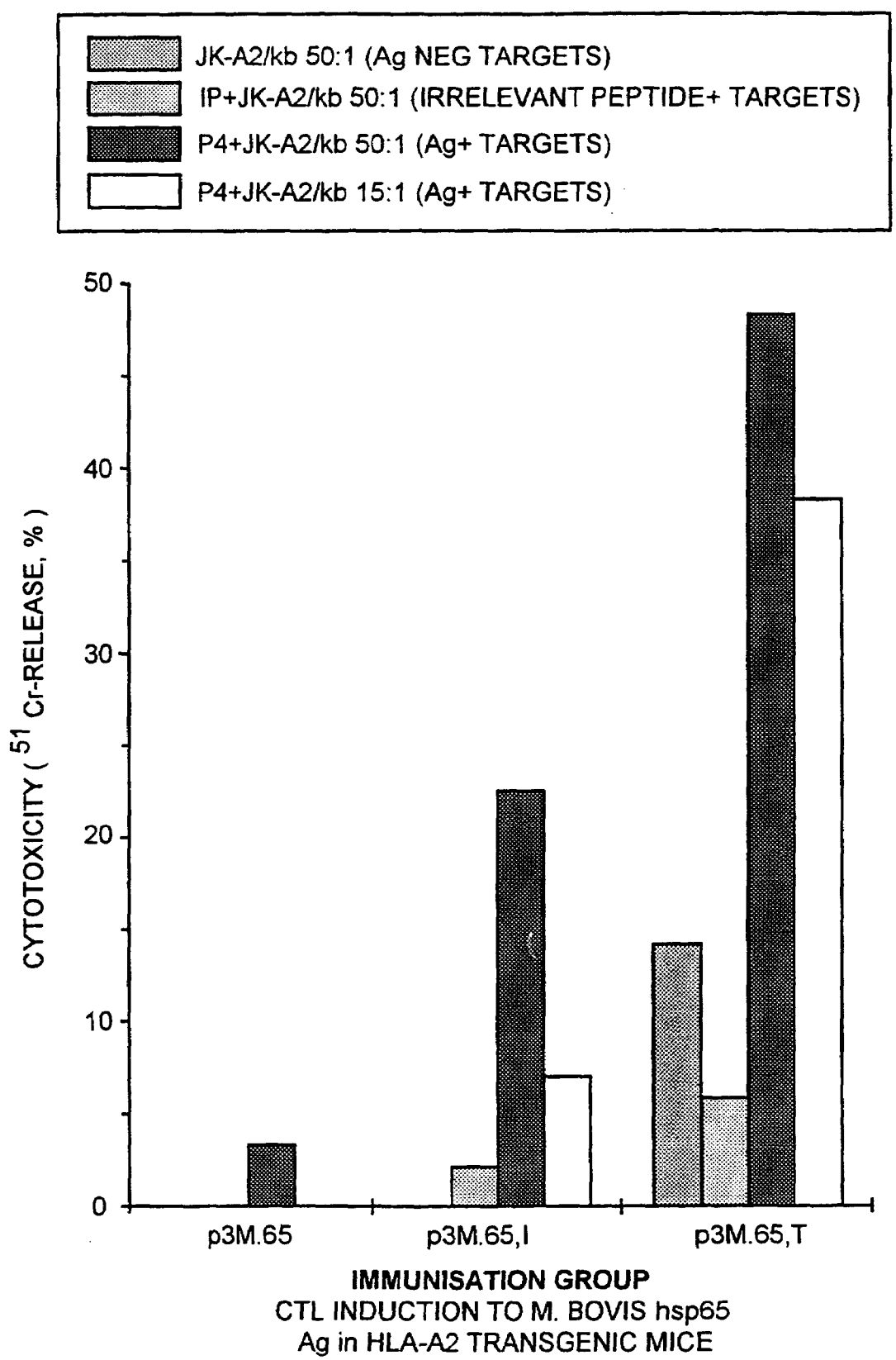

To investigate the effect of tucaresol on the specific cytotoxic T-cell (CTL) response induced by pDNA vaccination, we have immunised HLA A2 transgenic mice twice with either p3 M.65, p3M.65γ or p3M.65, T. Two weeks after the last immunisation splenocytes form the immunised mice were stimulated once with the HLA-A2 restricted peptide epitope derived from the mycobacterial hsp65 molecule, and the cultures tested for specific CTL activity against the HLA-A2/kb Jurkat (Jk-A2/kbds) cell line unpulsed or pulsed with the cognate peptide or with a control HLA A2 restricted influenza peptide. Splenocytes from mice immunised with p3M.65 and tucaresol (p3M.65,T) developed high CTL activity against target cells pulsed with the cognate M.hsp65 epitope while their lytic activity against Jk-A2/kb cells unpulsed or pulsed with the control influenza peptide was much lower (FIG. 6). In contrast, splenocytes from mice immunised with the p3M.65 without any co-stimulatory agent were almost totally inactive. The inclusion of the IFNγ plasmid together with the p3M.65 vaccine (p3M.65γ) enhanced the CTL activity of the splenocytes as compared to the activity of splenocytes derived from the mice immunised with p3M.65 only, but this cytotoxicity was only 30–50% of that observed with splenocytes form mice treated with tucaresol. We therefore conclude that tucaresol is a very efficient agent to enhance the development of specific CTL when given together with pDNA vaccination.

EXAMPLE 6

Effect of Tucaresol on Tumour Outgrowth Inhibition In Vivo Following Immunisation with a Plasmid Expressing the Epstein Barr Virus Nuclear Antigen 4 (EBNA-4)

Figure 7:
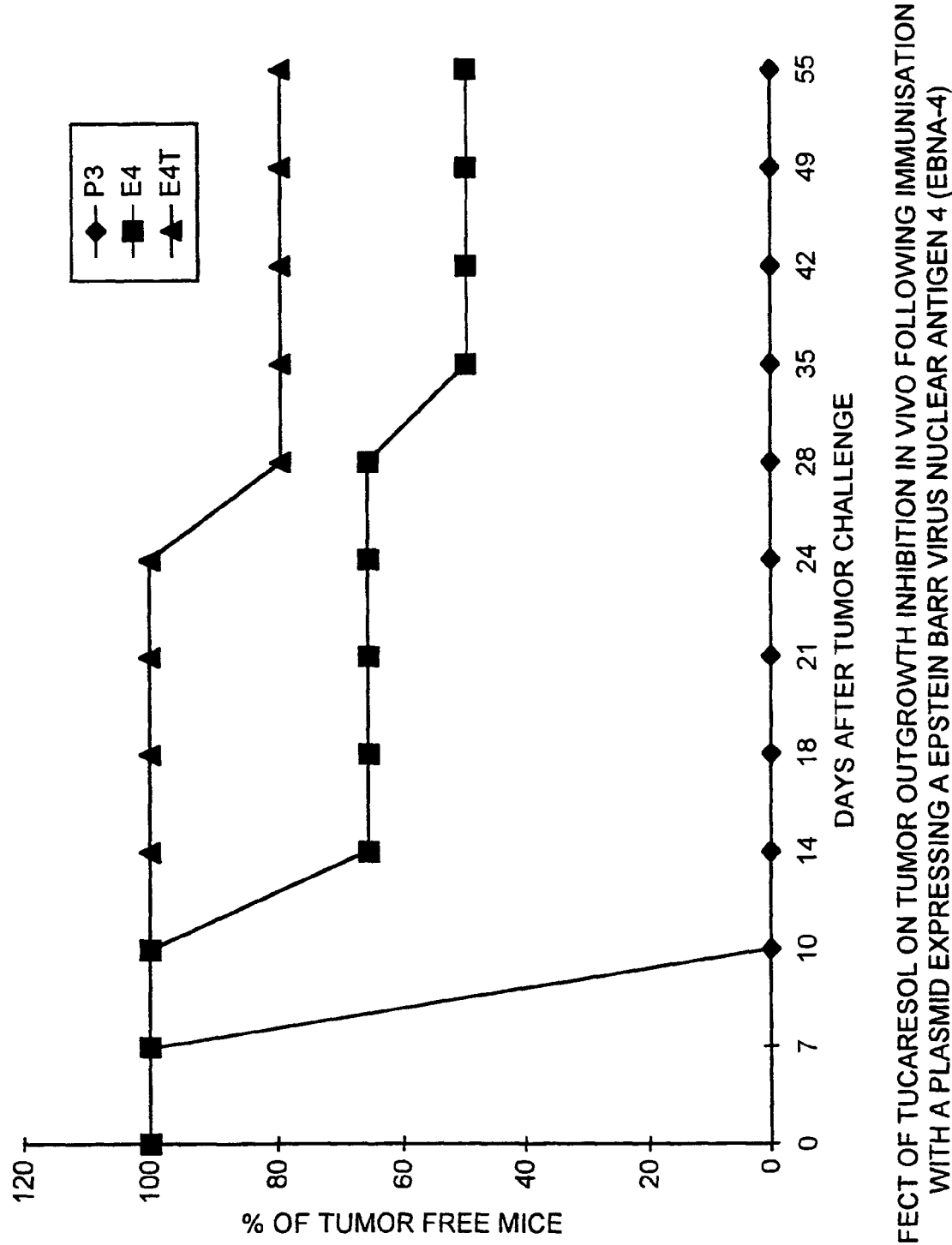

Epstein Barr virus has been implicated in some cancers. We analysed the effect of tucaresol on tumour outgrowth inhibition in vivo as a result of pDNA vaccination with a plasmid expressing EBNA-4 (FIG. 7). Mice were immunised by intramuscular injection with 40 μg of either control mock plasmid pCDNA3 (P3), plasmid expressing EBNA-4 (E4) or plasmid expressing EBNA-4 followed 1, 2, 3 and 4 days later with administration of 200 μg of tucaresol s.c.— i.e. 800 μg total tucaresol per mouse (E4T). This immunisation schedule was repeated 1 month and 2 months after the initial immunisation. Two weeks after the last immunisation mice were challenged with 104 S6C-E4 tumour cells s.c. Mice were sacrificed when the tumour reached a 20 mm diameter. FIG. 7 shows that tucaresol significantly enhances the ability of EBNA-4 to inhibit tumour outgrowth.

EXAMPLE 7

Effect of Tucaresol on CTL Cytokine Response Induced by Gene Gun DNA Immunisation in Mice.

The production of interferon gamma (IFNγ) by cytotoxic T lymphocytes (CTL) is a key measure of cell-mediated immune responses important in the elimination of viral infection.

Using Influenza NP Antigen (FIG. 8a)

C57BL/6 mice were immunised by gene gun with DNA plasmids encoding A/PR8/34 influenza virus nucleoprotein (pVAC1.PR) at two dose levels (10 & 100 ng) or empty vector. Spleens were collected 14 days post immunisation and splenocytes re-stimulated in vitro with an NP peptide (10 μM), recognised only by CD8 cytotoxic T-cells, together with recombinant human IL-2 (50 ng/ml). IFNγ positive cells per 10e6 splenocytes were detected by ELISPOT assay which measures the number of individual cells producing cytokine (mean±S.E.M.; n=3 mice). Tucaresol was administered to mice at the time of immunisation either subcutaneously (s.c.) (2×1 mg) at the site of intra-epidermal DNA vaccination, or by oral gavage (15 mg/kg) daily for 5 days beginning on the day of immunisation. Subcutaneous tucaresol produces a small but significant increase in the CTL cytokine response to immunisation while oral tucaresol produces a doubling of the response.

Using Epstein Barr Virus Nuclear Antigen 4 (EBNA-4) (FIG. 8b)

Mice were immunised by gene gun with DNA plasmids encoding EBNA-4 (E4) or empty vector (P3). 2 ug of DNA was administered per shot, giving two non overlapping shots per mouse. Tucaresol was administered to the mice (E4T) in 200 ug amounts subcutaneously on days 1, 2, 3 and 4. Mice were boosted after two months with the same immunisation and treatment schedule. Two weeks later splenocytes were stimulated in vitro with tumour cells expressing the EBNA-4 antigen (S6C-E4) or with antigen negative tumour cells (S6C-gpt) for 72 h. Supernatants were then collected and IFN-y titres were determined by specific ELISA. Tucaresol dramatically increased the production of IFNγ.

EXAMPLE 8

Effect of Tucaresol on Lytic CTL Response Induced by Gene Gun DNA Immunisation

Lysis of target cells by CD8 CTL is a principal mechanism in the elimination of viral infections by the immune system. Lytic CTL can be measured using target cells carrying viral peptide and labelled with europium.

Subcutaneous Administration of Tucaresol (FIG. 9a)

C57Bl/6 mice were immunised with plasmid DNA (10 ng) encoding the influenza virus nucleoprotein (NP) with and without tucaresol given sub-cutaneously (sc). Mice were killed 14 days post-immunisation and restimulated in-vitro (5 days) with irradiated splenocytes pulsed with virus (A/PR8/34). Standard europium release techniques were used to determine specific lysis of MHC-matched target cells (EL4 cells) pulsed with H-2 $D^b$-restricted NP peptide. Non-specific lysis was less than 15% for all controls. Tucaresol was given subcutaneously (1 mg) at the site of intrepidermal gene-gun immunisation.

Oral Administration of Tucaresol (FIG. 9b)

C57Bl/6 mice were immunised with plasmid DNA (10 ng) encoding the influenza virus nucleoprotein (NP) with and without tucaresol given orally. Mice were killed 14 days post-immunisation and restimulated in-vitro (5 days) with irradiated splenocytes pulsed with virus (A/PR8/34). Standard europium release techniques were used to determine specific lysis of EL4 cells pulsed with H-2$D^b$-restricted NP peptide. Non-specific lysis was less than 15% for all controls. Tucaresol (15 mg/kg) was given by oral gavage once daily for 5 days beginning on the day of immunisation.

Discussion of Experimental Results

We introduce herein a simple and very effective approach to enhance pDNA immunisation, based on providing a co-stimulatory signal to T-cells via Schiff base formation. Several of our observations demonstrate that this method is able to circumvent the problem of limitation in efficacy which commonly is encountered as a result of pDNA vaccination. These include an observed induction of a specific immune response in the majority of the immunised animals, while the approaches of using cytokine encoding vectors was considerably less efficient in that regard (data not shown). The enhancement was also associated with a significant quantitative increase in the response as compared to giving the pDNA vaccination alone or in combination with the pDNA expressing cytokine genes, and was observed both as increased specific antibody titres and as enhanced proliferative and cytotoxic T-cell responses.

The induction of an adequate immune response requires the participation of multiple components of the immune system, and pDNA immunisation fulfils this requirement as it induces both humoral and cellular responses including CTL responses, all of which were found to be enhanced by tucaresol. Moreover, while other modes of enhancing pDNA immunisation will lead to an antibody of a T-cell biased immune response, co-injection of tucaresol resulted in a general enhancement of both types of specific immunity including the enhancement of Th1 and Th2 associated antibody responses. The combination of pDNA vaccination and tucaresol can therefore be considered in conditions where either a cellular of antibody based immune response would be beneficial for the host.

There was a marked increase in the production of specific antibody production as also measured by the highest IgG: IgM ratio as compared to the other immunisation procedure (data not shown). This points out the potential advantage of using this procedure during the production of monoclonal antibodies.

The marked ability of tucaresol to enhance pDNA induced specific T-cell responses to hsp65, Influenza NP and EBNA-4, as detected by proliferation, cytokine production and cytotoxicity, is of particular importance. Protective immunity to mycobacterial infection is dependent on both $CD4^+$ T-cells with the capacity to secrete macrophage activating cytokines, including IFNγ and on cytotoxic $CD8^+$ cells which can eliminate infected macrophages. Protective immunity to EBV infection is dependent on $CD4^+$ and $CD8^+$ T-cell responses, and T-cell based immunotherapy against post-transplant transplant lymphoproliferative disorders has already proven to be efficient. Since pDNA vaccination combined with tucaresol favors both CD4 and CD8 mediated responses, as shown here, this is an attractive mode of vaccination to be applied in new T-cell vaccines against intra-cellular bacteria and viruses.

Tucaresol is a chemically well-defined molecule which has already been clinically tested. This should simplify the approval procedure of this drug in new pDNA-based vaccination protocols. Furthermore, as it was shown to be systematically active there is no need for local co-administration of pDNA and tucaresol, as shown here by combining intramuscular pDNA immunisation with subcutaneous injection of tucaresol. The combination of intradermal "ballistic" delivery of pDNA vaccination with oral administration of tucaresol may prove a very attractive mode of immunisation particularly under conditions where parenteral immunisations should be avoided due to risks of blood-borne infections or cultural stigmata associated with injections.

In summary, we present herein data that show for the first time the utility of using a Schiff base forming drug as a simple and effective method to augment the specific immune response induced by pDNA vaccination. These data are applicable for both clinical and industrial settings.

Experimental Methods

Plasmid Construction and Test

All genes were inserted in the pCDNA3 vector (Invitrogen BV, NV Leek, The Netherlands). *Mycobacterium bovis* hsp65 cDNA was excised from plasmid pRIB1300 (kindly provided by Dr. R. v d Zee, Utrecht University, Utrecht, The Netherlands) using Eco RI and Sal I and sub-cloned in the Eco RI and Xho I sites of pCDNA3 MCS. The identity and orientation of the gene in the resulting plasmid (p3M.65) were confirmed with restriction mapping. Expression and production of hsp protein was detected in the lysate of COS-7 transfected with p3M.65 by lipofection using Lipofectine (Life technologies, Paisley, Scotland). Lysates were electrophoresed on 12% SDS-PAGE gel, followed by Western Blotting on PVDF membrane (BioRad, CA) and immuno-detection by anti-Mycobacterial hsp65 specific monoclonal antibody DC-16 (kindly provided by Dr. Juraj Ivanyi, London, U.K.). This was then detected with a secondary alkaline phosphatase conjugated goat anti-mouse Ig (Southern Biotech, AL) and the blot was developed using the western blue substrate system (Promega, Madison, Wis.).

ELISA Procedures

Sera from immunised mice were collected and used in direct ELISA as described earlier. Recombinant mycobacterial hsp65 (kindly provided by Dr R. v d Zee) was used at a concentration of 4 µg/ml carbonate buffer to coat wells of 96 well plate (Maxisorp, Nunc, Denmark) overnight at 4° C. Sera were added in duplicate at 1:100 dilution, incubated overnight at 4° C. Binding antibodies were detected using IgG (preabsorbed against mouse IgM), IgG1 and IgG2a specific alkaline phosphatase conjugated goat anti-mouse sera (Southern Biotech).

Mice

HLA-A2*0201/Kb transgenic mice (kindly provided by Dr L. Sherman, Scripps Laboratories, San Diego, Calif.) used in this study have been described. These mice express a chimeric MHC class II molecule I which the α1 and α2 domains are of the HLA-A*0201 molecule while the α3 trans-membrane and cytoplasmic domains are of the mouse H2 Kb molecule. This construction permits the binding site of the mouse CD8 molecule on the T-cell to interact with the α3 domain of the chimeric molecule. The surface expression of the HLA-A*0201/Kb was confirmed using HLA-A*0201 specific FITC-conjugated monoclonal antibody (One Lambda, Ca) and assessed by flow cytometry using FACS-CAN (Becton Dickinson & Co., Mountain View, Calif.). C575BI/6 mice have been described. These mice have a defined influenza virus nucleoprotein CTL epitope. ACA (H-2f) mice were purchased from Jackson (Jackson Laboratory, Bar Harbor, Main). Mice were propagated and held in our SP environment in MTC animal house at the Karolinska Institute.

Immunisation

Genetic immunisation was accomplished by intra-muscular immunisation. Plasmids were prepared form LB ampicillin E. coli culture using Qiagen plasmid giga kit (Qiagen GmbH, Hilden, Germany). Concentrations and purity were determined using spectrophotometer and analytical gel electrophoresis. Mice were injected in the regenerating tibialis-anterior muscle according to the method of Davis et al using 20 µg pDNA/100 ul/muscle of either control plasmid (P3), EBNA-4 expressing plasmid plus control plasmid p3 (E4), p3M.65 expressing plasmid plus control plasmid p3 (p3M.65), p3M.65 plus GM-CSF expression plasmids (p3M.65G), or p3M.65 plus IFNγ expression plasmid (9p3M.65γ). Plasmids were mixed in equal molar quantities. Alternatively, immunisation was carried out by gene gun according to the method of Fynan et al (27) using 10 ng or 100 ng of DNA plasmid encoding A/PR8/34 influenza virus nucleoprotein (pVAC1.PR) or empty vector, or 2 ug of plasmid encoding EBNA-4 (E4) or control vector p3. Tucaresol treated mice were immunised with E4, p3M.65, or pVAC1.PR (E4,T p3M.65,t and pVAC1.NP PR(Tuc sc) respectively) and either injected at the same time with 1 mg tucaresol each sub-cutaneously or received daily injections of tucaresol 200 µg per mouse for a period of 4 days also sub-cutaneously. Mice received boosting two weeks after priming with the same dose.

Cell Lines

Jurkat A*0201/Kb(Jk-A2/kb), a human t-cell leukaemia 0HLA-A*0201 negative cell line stably transfected with HLA-A80201/Kb chimeric gene (kindly provided by Dr. W. M. Kast, Loyola University, Maywood Ill.). The S6C cell line was derived from a spontaneous mammary adenocarcinoma that has been originated in an ACA mouse. S6C-gpt and S6C-E4 are control plasmid and EBNA-4 transfectant respectively (kindly provided by Dr. George Klein, MTC, Karolinska Institute, Stockholm). All cell lines were maintained by passing in vivo in syngeneic ACA mice and in vitro in RPMI 1640 supplemented with 10% fetal bovine serum (FBS), 100 U/ml penicillin, 100 µg/ml streptomycin, 50 µM 2-mercaptoethanol, and 2 mM L-glutamine.

Proliferation Test

Splenocytes were harvested from immunised mice. A single cell suspension was prepared and cells were re-suspended in IMDM supplemented with 10% FBS and L-glu and antibiotics. Mixed splenocytes and tumor cell cultures (MSTC) were prepared by mixing $3\times10^6$ tumor cells per ml. Cultures were incubated for 5 days at 37° C. in 7.5% $CO_2$. One µCi of tritium labelled thymidine was added to each well of U-shaped bottom 96 well plates. Cells were further incubated for 18 hours in the same conditions as above and harvested and the amount of incorporated tritium labelled thymidine was measured using Beta Plate reader (Wallac, Turku, Finland). The test was done in triplicates and the stimulation index (SI) was calculated using the formula: SI=splenocyte proliferation towards the S6C-EBNA-4 transfectant (or EBNA-4 Vaccinia infected)/splenocyte proliferation toward S6C-gpt (or TK- Vaccinia infected) control transfectant.

Cytokine assays

Mixed splenocytes (from E4 immunised mice) and tumor cell cultures (MSTC) were prepared by mixing $3\times10^6$ splenocytes plus $3\times10^5$ tumor cells per ml. Supernatants were collected after 72 hours of culture and were tested for the presence of interferon gamma (IFNγ) and IL-4 using commercially available matched antibody pairs for mouse cytokines ELISA (Immunokontact, Bioggio, Switzerland) according to the manufacturer's instructions.

Specific CTL Line Generation and Cytotoxicity Assays.

Peptide specific CTL lines were prepared in 12-well plates as follows. Splenocytes, from immunised or control non-immunised mice were plated at $6\times10^6$ per well and co-cultured with $3\times10^6$ peptide pulsed (5 µg per ml P4) syngeneic splenocytes. After 6–8 days cell-mediated cytotoxicity was measured by $^{51}$Cr release as follows. One million target cells were incubated at 37° C. in the presence of 200 µCi sodium $^{51}$Cr chromate (Amersham, UK) for 1 hour, washed three times and re-suspended in compete medium at $10^5$ cells/ml in the presence of absence of 10 µg of the relevant (P4) or irrelevant (influenza NP 58–66) peptide. The test was performed by incubating $5\times10^3$ target cells at different effector to target ratios in triplicate wells at a final volume of 200 µl in V-bottomed 96 well plates. Cells were incubated for 4 hours at 37° C. after which supernatants were harvested and used to determine specific lysis using the following equation: percent specific release=100× (experimental release−spontaneous release)/(maximum release−spontaneous release).

It is to be understood that the present invention has been described by way of example only, and that modifications and/or alterations thereto, which would be obvious to a skilled person based upon the disclosure herein are also considered to fall within the scope and spirit of the invention, as defined in the appended claims.

REFERENCES

1. Donnelly J. et al, "DNA Vaccines" *Annu. Rev. Immunol.* 1997, 15: 617–48.
2. Donnelly, J. J., Friedman A., Martinez D., Montogomery, D. L., Shiver, J. W., Motzel, S. L., Ulmer, J. B., Liu, M. A. 1995. Preclinical efficacy of a prototype DNA vaccine-enhanced protection against antigenic drift in influenza-virus. *Nature Med.* 1:583–87.
3. Lu, S., Arthos, J., Montefiori, D.C., Yasutomi, Y., Manson, K., Mustafa, F., Johnson, E., Santoro, J. C., Wissink, J., Mullins, J. I., Haynes, J. R., Letvin, N. L., Wyand, M., Robinson, H. L. 1996. Simian immunodeficiency virus DNA vaccine trial in macaques. *J. Virol.* 70:3978–91.
4. Fuller, D. H. Haynes, J. R., 1994. A qualitative progression in HIV type 1 glycoprotein 120-specific cytotoxic cellular and humoral immune responses in mice receiving a DNA-based glycoprotein 120 vaccine. *AIDS Res. Hum. Retrovir.* 10:1433–41.
5. Krieg, A. M., Yi, A-K., Matson, S., Waldschmidt, T. J., Bishop, G. A., Teasdale, R., Koretsky, G. A. Klinman, D. M., 1995. CpG motifs in bacterial DNA trigger direct B-cell activation. *Nature* 374:546–48.
6. Messina, J. P., Gilkeson, G. S., Pisetsky, D. S., 1991. Stimulation of in vitro murine lymphocyte proliferation by bacterial DNA. *J. Immunol.* 147:1759–64.
7. Yamamoto, S., Yamamoto, T., Kataoka, T., Kuramoto, E., Yano, O., Tokunaga, T., 1992. Unique palindromic sequences in synthetic oligonucleotides are required to induce TNF and augment TNF-mediated natural killer activity. *J. Immunol.* 148:4072–76.
8. Tang, D. C., Devit, M., Johnston, S. A., 1992. Genetic immunisation is a simple method for eliciting an immune response. *Nature* 356:152–54.
9. Yankauckas, M. A., Morrow, J. E., Parker S. E., Abai, A., Rhodes, G. H., Dwarki, V. J., Gromkowski, S. H. 1993. Long-term antinucleoprotein cellular and humoral immunity is induced by intramuscular injection of plasmid DNA containing NP gene *DNA Cell Biol.* 12:771–76.
10. Wang, B., Boyer, J., Srikantan, V., Coney, L., Carrano, R., Phan, C., Merva, M., Dang, K., Agadjanyan, M., Gilbert L., Ugen, K. E., Williamson, W. V., Weiner, D. B. 1993. DNA inoculation induces neutralising immune-responses against human-immunodeficiency-virus type-1 in mice and nonhuman-primates. *DNA Cell Biol.* 12:799–805.
11. Cox, G., Zamb, T. J., Babiuk, L. A. 1993. Bovine herpesvirus-1-immune-responses in mice and cattle injected with plasmid DNA. *J. Virol.* 67:5664–67.
12. Davis, H. L., Michel, M. L., Whalen, R. G., 1993. DNA-based immunisation induces continuous secretion of hepatitis-b surface-antigen and high-levels of circulating antibody. *Human Mol. Genet.* 2:1847–51.
13. Ulmer, J. B., Donnelly, J. J. Parker, S. E., Rhodes, G. H, Felgner, P. L., Dwarki, V. J., Gromokowski, S. H., Deck, R. R., Dewitt, C. M., Friedman, A., Hawe, L. A., Leander, K. R., Martinez, D., Perry, H. C., Shiver, J. W., Montgomery, D. L., Liu, M. A., 1993. Heterologous protection against influenza by injection of DNA encoding a viral protein. *Science* 259:1745–49.
14. Kuhober, A., Pudollek, H—P, Reifenberg, K., Chisari, F. V., Schlicht, H-J, Reimann, J., Schirmbeck, R., 1996. DNA immunisation induces antibody and cytotoxic T cell-responses to hepatitis B core antigen in H-2b mice. *J. Immunol.* 156:3687–95.
15. Okuda, K., Bukawa, H., Hamajima, K., Kawamoto, S., Sekigawa, K. I., Yamada, Y., Tanaka, S. I., Ishii, N, Aoki, I., Nakamura, M., Yamamoto, H., Cullen, B. R., Fukushima, J., 1995. Induction of potent humoral and cell-mediated immune-responses following direct-injection of DNA encoding the HIV type-1 env and rev gene-products. *Aids Res. Human Retrovir.* 11:933–43.
16. Liu, M. A., Davies, M. E., Yasutomi, Y., Perry, H C., Letvin, N. L., Shiver, J. W., 1994. Immune responses to HIV generated by DNA vaccines. In *Retroviruses of Human AIDS and Related Animal Diseases*, ed. M. Girard, B. Dodet, pp. 197–200. Lyon: Fond. Mercel-Merieux.
17. Shiver, J. W., Perry, H. C., Davies, M. E., Freed, D. C., Liu, M. A., 1995. Cytotoxic T-lymphocyte and helper T cell responses following HIV polynucleotide vaccination. *Ann. N.Y. Acad. Sci.* 772:198–208.
18. Xiang, Z. Q., Ertl, H., 1995. Manipulation of the immune-response to a plasmid-encoded viral-antigen by coinoculation with plasmids expressing cytokines. *Immunity* 2:129–35.
19. Conry, R. M., Widera, G., Lobuglio, A. F., Fuller, J. T., Moore, S. E., Barlow, D. L., Turner, J., Curiel, D. T., 1996. Selected strategies to augment polynucleotide immunisation. *Gene Therapy* 3:67–74.
20. Tascon, R., Stavropoulos, E., Colston, M. J., Lowrie, D. B. 1996. Polynucleotide vaccination induces a significant protective immune response against Mycobacteria. In *Vaccines 96*, ed. F. Brown, R. M. Chanock, M. S. Ginsbert, R. A. Lerner, pp. 45–49. Cold Spring Harbor, N.Y.: Cold Spring Harbor Lab. Press.
21. Maniatis, T., Sambrook, J., Fritsch, E. F., "Molecular cloning: A Laboratory Manual", Cold Spring Harbour Laboratory, Cold Spring Harbour Press, Vols 1–3, $2^{nd}$ Edition, 1989.
22. Rhodes et al, "*Therapeutic Potentiation of the Immune System by Co-Stimulatory Schiff-Based-Forming Drug*," Nature, 377, pp 71–75, 1995.
23. Brohm W et al, "*Routes of Plasmid DNA Vaccination that Prime Murine Humoral and Cellular Immune Reponses*," Vaccine, Vol 16, No. 9/10, pp 949–954, 1998.
24. Remington's Pharmaceutical Sciences, Mack Publishing Company, Easton, Pa. (1985).
25. Vordermeier, H. M., Coombs, A. G. A., Jenkins, P. McGee, J. P., O'Haga, D. T. Davis, S. S. and Singh, M. Synthetic delivery systems for tuberculosis vaccines: immunolical evaluation of the *M. tuberculosis* 38 kDa protein entrapped in biodegradable PLG microparticles. Vaccine 13: 1576–1582 1995.
26. Haynes J R. McCabe DE. Swain W F. Wedera G. Fuller J T. Particle-mediated nucleic acid immunisation. Journal of Biotechnology. 44: 37–42, 1996.
27. Fynan, E. F., Webster, R. G., Fuller, D. H., Haynes J. T., Santoro, J. C., and Robinson, H. L., (1993) DNA vaccines: protective immunisations by parenteral, mucosal and gene-gun inoculatiions. Proc. Natl. Acad. Sci. USA 90:11478

The invention claimed is:

1. A method of vaccinating a mammal against a disease state, comprising administrating to said mammal, within an appropriate vector, a nucleotide sequence encoding an antigenic peptide associated with the disease state and not associated with a virus particle;

additionally administering to said mammal a Schiff base forming compound which enhances both humoral and cellular immune responses initiated by the antigenic peptide, the compound being selected from the group consisting of:

4-(2-formyl-3-hydroxyphenoxymethyl)benzoic acid;
5-(2-formyl-3-hydroxyphenoxy)pentanamide;
N,N-diethyl 5-(2-formyl-3-hydroxyphenoxy)pentanamide;
N-isopropyl 5-(2-formyl-3-hydroxyphenoxy)pentanamide;
ethyl 5-(2-formyl-3-hydroxyphenoxy)pentanoate;
5-(2-formyl-3-hydroxyphenoxy)pentanonitrile;
(±)-5-(2-formyl-3-hydroxyphenoxy)-2-methylpentanoic acid;
5-(2-formyl-3-hydroxyphenoxy)-2,2-dimethylpentanoic acid;
methyl 3-(2-formyl-3-hydroxyphenoxy)methylbenzoate;
3-(2-formyl-3-hydroxyphenoxy)methylbenzoic acid;
benzyl 5-(2-formyl-3-hydroxyphenoxy)pentanoate;
5-[4-(2-formyl-3-hydroxyphenoxy)-N-butyl]tetrazole;
7-(2-formyl-3-hydroxyphenoxy)heptanoic acid;
5-(2-formyl-3-hydroxy-4-n-propoxyphenoxy)pentanoic acid;
5-(4,6-dichloro-2-formyl-3-hydroxyphenoxy)pentanoic acid;
5-(2-formyl-3-hydroxyphenoxy)-N-methylsulphonylpentanamide;
ethyl 4-(2-formyl-3-hydroxyphenoxymethyl)benzoate;
5-(4-chloro-2-formyl-3-hydroxyphenoxy)pentanoic acid;
5-(3-acetylamino-2-fomyl phenoxy)pentanoic acid;
Aminoguanidine;
4-(2-formyl-3-hydroxyphenoxy)butanoic acid;
6-(2-formyl-3-hydroxyphenoxy)hexanoic acid;
ethyl 4-(3-acetylaminio-2-formylphenoxymethyl)benzoate;
4-(3-acetylamino-2-formylphenoxymethyl)benzoic acid;
2-(2-formyl-3-hydroxyphenoxymethyl)benzoic acid;
5-[4-(2-formyl-3-hydroxyphenoxymethyl)phenyl]tetrazole;
5-(2-formyl-3-hydroxy-4-methoxyphenoxy)pentanoic acid;
3-(2-formyl-3-hydroxyphenoxy)propionitrile;
4-Hydroxyphenylacetaldehyde;
Phenylacetaldehyde;
4-Methoxyphenylacetaldehyde;
1-hydroxy-2-phenylpropane;
3-Phenylproponionaldeyde;
4-Nitrobenzaldehyde;
Methyl 4-formylbenzoate;
4-Chlorobenzaldehyde;
4-Methyloxybenzaldehyde;
4-Methylbenzaldehyde;
8,10-Dioxoundecanoic acid;
4,6-Dioxoheptanoic acid;
Pentanedione;
5-methoxy-1-tetralone;
6-methoxy-1-tetralone;
7-methoxy-1-tetralone;
2-tetralone;
3-hydroxy-1-(4-methoxyphenyl)-3-methyl-2-butanone;
2',4'-dihydroxy-2-(4-methoxyphenyl)acetophenone;
2-hydroxy-1-(4-methyoxyphenyl)-pent-2ene-4one;
Naringenin 4',5,6-trihydroxyflavonone;
4'-methoxy-2-(4-methoxyphenyl)acetophenone;
6,7-dihydroxycoumarin;
7-methoxy-2-tetralone;
6,7-dimethoxy-2-tetralone;
6-hydroxy-4-methylcoumarin;
Homogentisic acid gamma lactone;
6-hydroxy-1,2-naphthoquinone;
8-methoxy-2-tetralone;

and physiologically acceptable salts thereof, where appropriate.

2. The method according to claim 1 wherein administration of the compound takes place on between one and seven occasions, between 14 days prior to and 14 days post administration of the nucleotide sequence.

3. The method according to claim 1 wherein administration of the compound takes place on between one and seven occasions, between 7 days prior to and 7 days post administration of the nucleotide sequence.

4. The method according to claim 1 wherein administration of the compound takes place between 24 hours prior to and 24 hours post administration of the nucleotide sequence.

5. The method according to claim 1 wherein administration of the compound is simultaneous with administration of the nucleotide sequence.

6. The method according to claim 1 wherein administration of the compound and the nucleotide sequence is repeated between 1 and 4 times, at intervals of between 1 day and about 18 months.

7. The method according to claim 1 wherein administration of the nucleotide sequence is via the oral, nasal, pulmonary, intramuscular, subcutaneous or intradermal route.

8. The method according to claim 7 wherein the nucleotide sequence is administered using a gene-gun delivery technique.

9. The method according to claim 1 wherein administration of the compound is via the oral, nasal, pulmonary, intramuscular, subcutaneous, intradermal or topical route.

10. The method according to claim 9 wherein the compound is administered using a gene-gun delivery technique.

11. The method according to claim 1 wherein the compound is administered at a dose of between 0.1 mg/kg and 100 mg/kg per administration.

12. The method according to claim 1 wherein the mammal is a human.

13. The method according to claim 1 wherein the compound is 4-(2-formyl-3-hydroxyphenoxymethyl)benzoic acid.

14. A combination of components for separate, sequential or concomitant administration in a method of vaccinating a mammal against a disease state, comprising administrating to said mammal, within an appropriate vector, a nucleotide sequence encoding an antigenic peptide associated with the disease state and not associated with a virus particle;

additionally administering to said mammal a Schiff base forming compound which enhances both humoral and cellular immune responses initiated by the antigenic peptide, the compound being selected from the group consisting of:

4-(2-formyl-3-hydroxyphenoxymethyl)benzoic acid;
5-(2-formyl-3-hydroxyphenoxy)pentanamide;
N,N-diethyl 5-(2-formyl-3-hydroxyphenoxy)pentanamide;

N-isopropyl 5-(2-formyl-3-hydroxyphenoxy)pentanamide;
ethyl 5-(2-formyl-3-hydroxyphenoxy)pentanoate;
5-(2-formyl-3-hydroxyphenoxy)pentanonitrile;
(±)-5-(2-formyl-3-hydroxyphenoxy)-2-methylpentanoic acid;
5-(2-formyl-3-hydroxyphenoxy)-2,2-dimethylpentanoic acid;
methyl 3-(2-formyl-3-hydroxyphenoxy)methylbenzoate;
3-(2-formyl-3-hydroxyphenoxy)methylbenzoic acid;
benzyl 5-(2-formyl-3-hydroxyphenoxy)pentanoate;
5-[4-(2-formyl-3-hydroxyphenoxy)-N-butyl]tetrazole;
7-(2-formyl-3-hydroxyphenoxy)heptanoic acid;
5-(2-formyl-3-hydroxy-4-n-propoxyphenoxy)pentanoic acid;
5-(4,6-dichloro-2-formyl-3-hydroxyphenoxy)pentanoic acid;
5-(2-formyl-3-hydroxyphenoxy)-N-methylsulphonylpentanamide;
ethyl 4-(2-formyl-3-hydroxyphenoxymethyl)benzoate;
5-(4-chloro-2-formyl-3-hydroxyphenoxy)pentanoic acid;
5-(3-acetylamino-2-fomyl phenoxy)pentanoic acid;
Aminoguanidine;
4-(2-formyl-3-hydroxyphenoxy) butanoic acid;
6-(2-formyl-3-hydroxyphenoxy)hexanoic acid;
ethyl 4-(3-acetylaminio-2-formylphenoxymethyl)benzoate;
4-(3-acetylamino-2-formylphenoxymethyl)benzoic acid;
2-(2-formyl-3-hydroxyphenoxymethyl)benzoic acid;
5-[4-(2-formyl-3-hydroxyphenoxymethyl)phenyl]tetrazole;
5-(2-formyl-3-hydroxy-4-methoxyphenoxy) pentanoic acid;
3-(2-formyl-3-hydroxyphenoxy)propionitrile;
4-Hydroxyphenylacetaldehyde;
Phenylacetaldehyde;
4-Methoxyphenylacetaldehyde; jkhu
1-hydroxy-2-phenylpropane;
3-Phenylproponionaldeyde;
4-Nitrobenzaldehyde;
Methyl 4-formylbenzoate;
4-Chlorobenzaldehyde;
4-Methyloxybenzaldehyde;
4-Methylbenzaldehyde;
8,10-Dioxoundecanoic acid;
4,6-Dioxoheptanoic acid;
Pentanedione;
5-methoxy-1-tetralone;
6-methoxy-1-tetralone;
7-methoxy-1-tetralone;
2-tetralone;
3-hydroxy-1-(4-methoxyphenyl)-3-methyl-2-butanone;
2',4'-dihydroxy-2-(4-methoxyphenyl)acetophenone;
2-hydroxy-1-(4-methyoxyphenyl)-pent-2ene-4one;
Naringenin 4',5,6-trihydroxyflavonone;
4'-methoxy-2-(4-methoxyphenyl)acetophenone;
6,7-dihydroxycoumarin;
7-methoxy-2-tetralone;
6,7-dimethoxy-2-tetralone;
6-hydroxy-4-methylcoumarin;
Homogentisic acid gamma lactone;
6-hydroxy-1,2-naphthoquinone;
8-methoxy-2-tetralone;
and physiologically acceptable salts thereof, where appropriate; wherein the combination comprises the nucleotide sequence encoding for an antigenic peptide and the compound which enhances both humoral and cellular immune responses initiated by the antigenic peptide.

15. A method of vaccinating a mammal against a disease state, comprising administrating to said mammal, within an appropriate vector, a nucleotide sequence encoding an antigenic peptide associated with the disease state; additionally administering to said mammal a Schiff base forming compound which enhances at least Th1 and Th2 associated responses initiated by the antigenic peptide, the compound being selected from the group consisting of:
4-(2-formyl-3-hydroxyphenoxymethyl)benzoic acid;
5-(2-formyl-3-hydroxyphenoxy)pentanamide;
N,N-diethyl 5-(2-formyl-3-hydroxyphenoxy)pentanamide;
N-isopropyl 5-(2-formyl-3-hydroxyphenoxy)pentanamide;
ethyl 5-(2-formyl-3-hydroxyphenoxy)pentanoate;
5-(2-formyl-3-hydroxyphenoxy)pentanonitrile;
(±)-5-(2-formyl-3-hydroxyphenoxy)-2-methylpentanoic acid;
5-(2-formyl-3-hydroxyphenoxy)-2,2-dimethylpentanoic acid;
methyl 3-(2-formyl-3-hydroxyphenoxy)methylbenzoate;
3-(2-formyl-3-hydroxyphenoxy)methylbenzoic acid;
benzyl 5-(2-formyl-3-hydroxyphenoxy)pentanoate;
5-[4-(2-formyl-3-hydroxyphenoxy)-N-butyl]tetrazole;
7-(2-formyl-3-hydroxyphenoxy)heptanoic acid;
5-(2-formyl-3-hydroxy-4-n-propoxyphenoxy)pentanoic acid;
5-(4,6-dichloro-2-formyl-3-hydroxyphenoxy)pentanoic acid;
5-(2-formyl-3-hydroxyphenoxy)-N-methylsulphonylpentanamide;
ethyl 4-(2-formyl-3-hydroxyphenoxymethyl)benzoate;
5-(4-chloro-2-formyl-3-hydroxyphenoxy)pentanoic acid;
5-(3-acetylamino-2-fomyl phenoxy)pentanoic acid;
Aminoguanidine;
4-(2-formyl-3-hydroxyphenoxy)butanoic acid;
6-(2-formyl-3-hydroxyphenoxy)hexanoic acid;
ethyl 4-(3-acetylaminio-2-formylphenoxymethyl)benzoate;
4-(3-acetylamino-2-formylphenoxymethyl)benzoic acid;
2-(2-formyl-3-hydroxyphenoxymethyl)benzoic acid;
5-[4-(2-formyl-3-hydroxyphenoxymethyl)phenyl]tetrazole;
5-(2-formyl-3-hydroxy-4-methoxyphenoxy)pentanoic acid;
3-(2-formyl-3-hydroxyphenoxy)propionitrile;
4-Hydroxyphenylacetaldehyde;
Phenylacetaldehyde;
4-Methoxyphenylacetaldehyde;
1-hydroxy-2-phenylpropane;
3-Phenylproponionaldeyde;
4-Nitrobenzaldehyde;
Methyl 4-formylbenzoate;
4-Chlorobenzaldehyde;
4-Methyloxybenzaldehyde;
4-Methylbenzaldehyde;
8,10-Dioxoundecanoic acid;
4,6-Dioxoheptanoic acid;
Pentanedione;
5-methoxy-1-tetralone;
6-methoxy-1-tetralone;
7-methoxy-1-tetralone;
2-tetralone;
3-hydroxy-1-(4-methoxyphenyl)-3-methyl-2-butanone;
2',4'-dihydroxy-2-(4-methoxyphenyl)acetophenone;

2-hydroxy-1-(4-methyoxyphenyl)-pent-2ene-4one;
Naringenin 4',5,6-trihydroxyflavonone;
4'-methoxy-2-(4-methoxyphenyl)acetophenone;
6,7-dihydroxycoumarin;
7-methoxy-2-tetralone;
6,7-dimethoxy-2-tetralone;
6-hydroxy-4-methylcoumarin;
Homogentisic acid gamma lactone;
6-hydroxy-1,2-naphthoquinone;
8-methoxy-2-tetralone;
and physiologically acceptable salts thereof, where appropriate.

16. The method according to claim 15 wherein the compound is 4-(2-formyl-3-hydroxyphenoxymethyl)benzoic acid.

17. The method according to claim 1 wherein the vector which comprises the nucleotide sequence encoding the antigenic peptide is administered in a naked form.

18. The method according to claim 1 wherein the vector which comprises the nucleotide sequence encoding the antigenic peptide is encapsulated by liposomes or within polylactide co-glycolide particles.

19. The combination according to claim 14 wherein the vector which comprises the nucleotide sequence encoding the antigenic peptide is administered in a naked form.

20. The combination according to claim 14 wherein the vector which comprises the nucleotide sequence encoding the antigenic peptide is encapsulated by liposomes or within polylactide co-glycolide particles.

21. The method according to claim 15 wherein administration of the compound takes place on between one and seven occasions, between 14 days prior to and 14 days post administration of the nucleotide sequence.

22. The method according to claim 15 wherein administration of the compound takes place on between one and seven occasions, between 7 days prior to and 7 days post administration of the nucleotide sequence.

23. The method according to claim 15 wherein administration of the compound takes place between 24 hours prior to and 24 hours post administration of the nucleotide sequence.

24. The method according to claim 15 wherein administration of the compound is simultaneous with administration of the nucleotide sequence.

25. The method according to claim 15 wherein administration of the compound and the nucleotide sequence is repeated between 1 and 4 times, at intervals of between 1 day and about 18 months.

26. The method according to claim 15 wherein administration of the nucleotide sequence is via the oral, nasal, pulmonary, intramuscular, subcutaneous or intradermal route.

27. The method according to claim 26 wherein the nucleotide sequence is administered using a gene-gun delivery technique.

28. The method according to claim 15 wherein administration of the compound is via the oral, nasal, pulmonary, intramuscular, subcutaneous, intradermal or topical route.

29. The method according to claim 28 wherein the compound is administered using a gene-gun delivery technique.

30. The method according to claim 15 wherein the compound is administered at a dose of between 0.1 mg/kg and 100 mg/kg per administration.

31. The method according to claim 15 wherein the mammal is a human.

32. The method according to claim 15 wherein the vector which comprises the nucleotide sequence encoding the antigenic peptide is administered in a naked form.

33. The method according to claim 15 wherein the vector which comprises the nucleotide sequence encoding the antigenic peptide is encapsulated by liposomes or within polylactide co-glycolide particles.

* * * * *